United States Patent
Holmberg

(10) Patent No.: US 7,279,285 B2
(45) Date of Patent: Oct. 9, 2007

(54) METHOD OF REVERSIBLY DISRUPTING A CONJUGATE COMPRISING A BIOTIN COMPOUND AND A BIOTIN-BINDING COMPOUND

(75) Inventor: Anders Holmberg, Stockholm (SE)

(73) Assignee: Magnetic Biosolutions AB, Stockholm (SE)

(*) Notice: Subject to any disclaimer, the term of this patent is extended or adjusted under 35 U.S.C. 154(b) by 413 days.

(21) Appl. No.: 10/470,846

(22) PCT Filed: Feb. 1, 2002

(86) PCT No.: PCT/GB02/00466

§ 371 (c)(1), (2), (4) Date: Jul. 31, 2003

(87) PCT Pub. No.: WO02/061428

PCT Pub. Date: Aug. 8, 2002

(65) Prior Publication Data

US 2004/0077024 A1 Apr. 22, 2004

Related U.S. Application Data

(60) Provisional application No. 60/266,524, filed on Feb. 5, 2001.

(30) Foreign Application Priority Data

Feb. 1, 2001 (GB) .................. 0102568.3

(51) Int. Cl.
*G01N 33/53* (2006.01)
*C12Q 1/68* (2006.01)
(52) U.S. Cl. .......................... 435/7.1; 435/6
(58) Field of Classification Search .......... None
See application file for complete search history.

(56) References Cited

U.S. PATENT DOCUMENTS

| 5,395,856 | A | 3/1995 | Haase | 521/25 |
|---|---|---|---|---|
| 6,022,688 | A | 2/2000 | Jurinke et al. | 435/6 |
| 6,303,309 | B1 | 10/2001 | Jurinke et al. | 435/6 |

FOREIGN PATENT DOCUMENTS

| EP | 0 456 304 A1 | 11/1991 |
|---|---|---|
| WO | WO97/00329 A2 | 1/1997 |
| WO | WO 00/70073 A1 | 11/2000 |
| WO | WO 01/51067 A1 | 7/2001 |

OTHER PUBLICATIONS

Tong et al., "Solid-Phase Method for the Purification of DNA Sequencing Reactions," *Anal. Chem.* 1992, pp. 2672-2677, vol. 64. American Chemical Society.
Ding et al., "Temperature Control of Biotin Binding and Release with A Streptavidin-Poly(N-isopropylacrylamide) Site-Specific Conjugate," *Bioconjugate Chemistry*, 1999, pp. 395-400, vol. 10. American Chemical Society.
Morris et al., "Affinity Precipitation of Proteins by Polyligands," *Biotechnology and Bioengineering*, 1993, pp. 991-997, vol. 41, John Wiley & Sons, Inc.
Garret-Flaudy, et al., "Use of the Avidin (Imino)biotin System as a General Approach to Affinity Precipitation," *Biotechnology and Bioengineering*, 2001, pp. 223-234, vol. 71. John Wiley & Sons, Inc.
Foulon et al., "Preparation and Biological Evaluation of an Astatine-211 Labeled Biotin Conjugate: Biotinyl-3-[$^{211}$At]astatoanilide," *Nuclear Medicine and Biology*, 1997, pp. 135-143, vol. 24. Elsevier Science Inc.
Green et al., "The Kinetics of Biotin Binding-The Affinity for Avidin," *Biomolecular Engineering*, May 2000, p. 170, vol. 16. Abstract XP-002226761.

*Primary Examiner*—James Martinell
(74) *Attorney, Agent, or Firm*—Rothwell, Figg, Ernst & Manbeck

(57) ABSTRACT

The present invention relates to a method of disrupting a conjugate comprising a biotin compound and a biotin-binding compound, said method comprising the step of contacting said conjugate with an effective amount of a substantially aqueous solution under conditions such that the conjugate is disrupted, preferably reversibly disrupted, thereby forming a biotin compound and a biotin-binding compound. In particular, the invention relates to a method of reversibly releasing a biotinylated moiety from a streptavidin (or avidin) coated support. Uses of the methods in techniques of detection, identification, determination, purification, separation and/or isolation of target proteins or nucleic acid molecules are also encompassed by the present invention.

20 Claims, 27 Drawing Sheets

PCR with one biotinylated primer
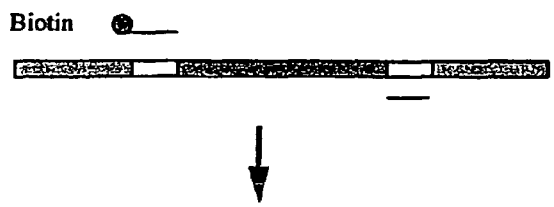
Figure 26
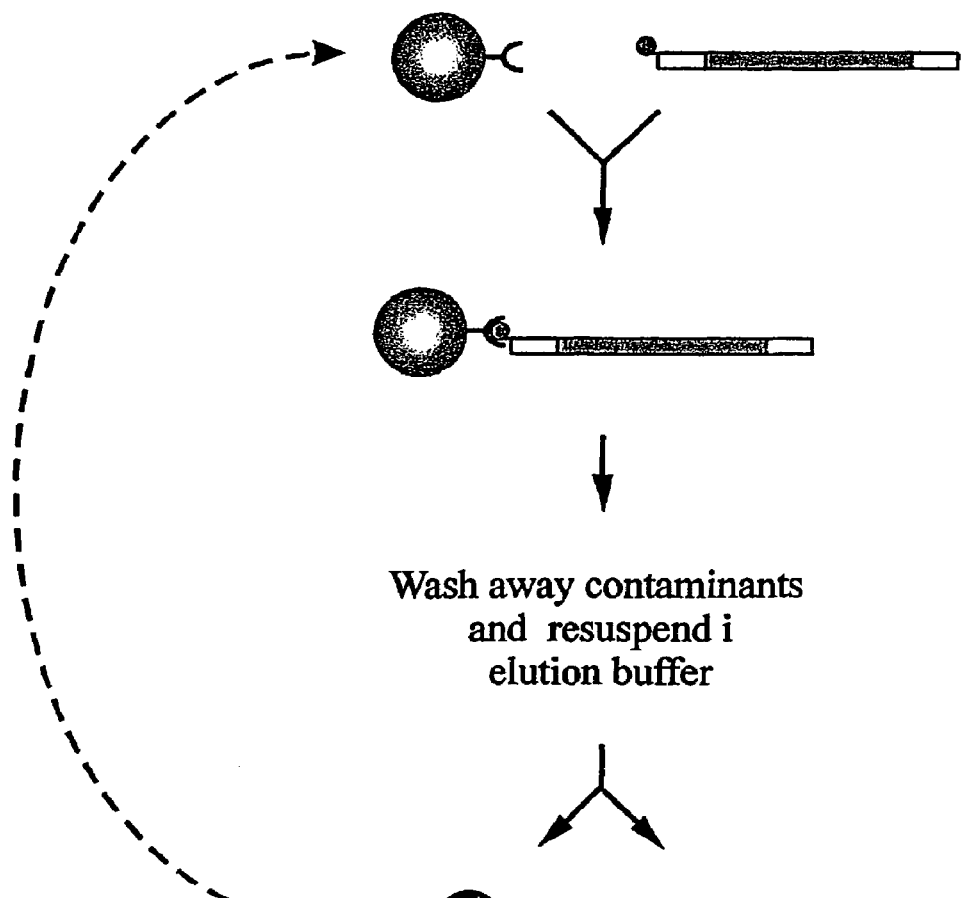
Bind to streptavidin coated
magnetic beads
Wash away contaminants
and resuspend i
elution buffer
Elute off purified dsDNA
and regenerate beads

METHOD OF REVERSIBLY DISRUPTING A CONJUGATE COMPRISING A BIOTIN COMPOUND AND A BIOTIN-BINDING COMPOUND

This application is a filing under 35 U.S.C. 371 of PCT/GB02/00466, which claims priority from GB 0102568.3, filed Feb. 1, 2001 and claims priority under 35 U.S.C. 119(e) of U.S. provisional application 60/266,524, filed Feb. 5, 2001.

BACKGROUND OF THE INVENTION

1. Field of the Invention

The present invention relates to the release of bound biotin from a biotin-binding compound such as streptavidin (or avidin). In particular, the invention relates to a method of reversibly releasing a biotinylated moiety from a streptavidin (or avidin) coated support.

The strong interaction between streptavidin (or avidin) and biotin (cis-hexahydro-2-oxo-1H-thieno[3,4]imidazole-4-pentanoic acid) is well known. Indeed, the binding between streptavidin and biotin (dissociation constant, $K_d$ approx. $10^{-15}$M) is regarded as one of the strongest known, non-covalent, biological interactions. The bond forms very rapidly and is considered to be stable under a wide range of pH, temperature and other denaturing conditions (Savage et al., Avidin-Biotin Chemistry: A Handbook, 1992:1-23, Rockford, Pierce Chemical Company). This has led to diverse and widespread applications using streptavidin-biotin or avidin-biotin technology.

2. Description of Related Art

Biotin-streptavidin is one of the most widely used affinity bindings in molecular, immunological and cellular assays. Streptavidin can be detected and quantitated with a high degree of sensitivity in such complexes, for example by labelling it with enzymes or with fluorescent, chemiluminescent or radioactive agents. Labelled streptavidin has, for example, been used to detect proteins on a cell surface, to visualize and quantitate blots, and to perform an enzyme-linked immunosorbent assay ELISA.

Streptavidin can also be readily immobilised at surfaces to capture biotinylated moieties, e.g. biotinylated molecules or cells. Such surfaces are used to detect and separate molecules or cells of interest from complex mixtures. The streptavidin-biotin interaction has thus found use in many of the separation, purification and isolation procedures known in the art, for example affinity chromatography, etc.

Immobilisation, particularly of oligonucleotides and nucleic acids, is frequently used in many molecular biological procedures and many of the commonly-used techniques, e.g. sequencing, in vitro amplifications, cDNA preparation, template preparation, etc., as well as nucleic acid purification, have been adapted for use on a solid phase, for example on a streptavidin-coated support. One particular area in which this is used is in the isolation of polymerase chain reaction (PCR) products, for example using streptavidin-immobilised magnetic microbeads (Hultman et al., Nucleic Acids Res. 17:4937-4946, 1989). This method is of great interest since it generally provides good yields and is easy to automate compared to traditional methods for purification of cycle sequencing products which often employ precipitation and/or centrifugation steps.

Most applications which use the biotin-streptavidin (or avidin) linkage rely on the essentially irreversible binding of biotin and streptavidin (or avidin). However, there are many cases in which release of bound biotin is desirable, e.g. to recover biotinylated molecules or cells.

A number of alternative strategies to disrupt or reverse the biotin-streptavidin linkage have previously been reported (Lee et al., Anal Biochem. 206:206-207, 1992, Elgar et al., DNA Sequence 2:219-226, 1992, and Conrad et al., Nucleic Acids Res. 20:6423-6424, 1992). However, these require harsh conditions, e.g. boiling in high salt conditions or use of formamide and EDTA heated to 94° C. for several minutes (Tong et al., Anal. Chem. 64:2672-2677, 1992), to achieve partial or complete bond disruption. Not only are such conditions generally harmful to any bound moiety (e.g. a protein or nucleic acid molecule), but these also result in denaturing of the biotin and/or streptavidin molecules. A denatured streptavidin molecule cannot be re-used. Moreover, since proteins can only be recovered under denaturing conditions these are inappropriate for the purification of delicate proteins. The use of denaturing conditions to reverse the biotin-streptavidin linkage is therefore undesirable, especially in bioseparations.

U.S. Pat. No. 5,387,505 describes a method for the separation of a complex comprising a biotinylated target nucleic acid and avidin-coated polymeric particles. This method involves heating of the complex to temperatures of at least 65° C., e.g. 85-100° C., in the presence of a salt wash solution comprising inter alia sodium chloride, SDS and EDTA. These harsh conditions similarly result in denaturation of the biotin and avidin molecules such that these cannot be re-used.

Others have reported various approaches to disrupt the biotin-streptavidin complex under more mild conditions, such as introducing light sensitive biotin phosphoramidites (Olejnik et al., Nucleic Acids Res. 24:361-366, 1996) or the use of polymer conjugates together with streptavidin mutants that yields temperature or pH dependent release. For example, Ding et al. (Bioconjugate Chem. 10:395-400, 1999) have conjugated a temperature-sensitive polymer, poly(N-isopropylacrylamide) (NIPAAm), to a genetically engineered streptavidin (SAv) to produce a conjugate capable of binding biotin at room temperature or lower and releasing bound biotin at 37° C. This conjugate can repeatedly bind and release biotin as the temperature is cycled through the lower critical solution temperature (LCST) of the polymer. More recently, Bulmus et al. (Bioconjugate Chem. 11:78-83, 2000) conjugated a pH-sensitive polymer (a copolymer of NIPPAm and acrylic acid) to the same specific site on the genetically engineered SAv molecule. Lowering the pH was found to cause the polymer to collapse leading to blockage of biotin binding, whereas raising the pH caused the polymer to fully hydrate thereby permitting biotin to bind.

However, none of the methods so far proposed for the reversible binding between biotin and streptavidin readily lends itself to use in DNA sequencing methods, for example using capillary or slab gel DNA sequencing instrumentation. Consequently, there is a continuing need in the art for alternative methods for reversibly and reliably disrupting the binding of biotin and streptavidin (or avidin), in particular such methods which use relatively mild conditions and so facilitate re-use of a streptavidin-coated support, e.g. in automated systems for DNA sequencing.

SUMMARY OF THE INVENTION

Contrary to previous findings, it has now been found that a reversible disruption of the biotin-streptavidin or biotin-avidin interaction can be achieved using a substantially aqueous solution, for example under controlled temperature conditions. This finding extends to the disruption of the interaction between a biotin compound and any biotin-binding compound.

Viewed from one aspect the invention thus provides a method of disrupting a conjugate comprising a biotin compound and a biotin-binding compound, said method comprising the step of contacting (e.g. incubating) said conjugate with an effective amount of a substantially aqueous solution under conditions such that the conjugate is disrupted, preferably reversibly disrupted, thereby forming a biotin compound and a biotin-binding compound.

In a preferred aspect the invention provides a method of disrupting a conjugate comprising a biotin-streptavidin or biotin-avidin linkage, said method comprising the step of contacting (e.g. incubating) said conjugate with an effective amount of a substantially aqueous solution whereby to effect cleavage, preferably reversible cleavage of said linkage.

Thus, a preferred embodiment of the method of the invention essentially provides for reversible binding of biotin to a biotin-binding compound, e.g. streptavidin (or avidin). In this context, reversible is intended to mean not only that binding of the partners is reversible, i.e. that these may be separated, but also that the linkage may be reformed thereafter. As used herein the terms "reversible" or "reversibly", etc. are thus intended to mean that biotin or a biotinylated moiety can be cleaved, released or detached from a biotin-binding compound, e.g. streptavidin (or avidin), without substantial denaturation or inactivation of either molecule of the binding pair, or of any moiety to which either of these may be bound. Following release, the capacity of biotin to again bind to the biotin-binding compound, e.g. streptavidin (or avidin), is thus not compromised. However, as in any biological system, a degree of tolerance is to be allowed for such that a minor or negligible degree of denaturation or inactivation can be tolerated.

DETAILED DESCRIPTION OF THE INVENTION

The terms "cleaving", "releasing", or "disrupting" are used herein interchangeably and are intended to mean physical separation or detachment or dissociation of the partners of the binding pair, i.e. biotin (or a biotinylated moiety) and the biotin-binding compound, e.g. streptavidin (or avidin).

The terms "conjugate" and "complex" as used herein refer to any conjugate or complex comprising a biotin compound and a biotin-binding compound, e.g. a complex of biotin or a biotinylated moiety with streptavidin (avidin), in which the biotin compound and biotin-binding compound are linked by non-covalent bonding.

The terms "biotin" or "biotin compound" as used herein are intended to refer to biotin (cis-hexahydro-2-oxo-1H-thieno[3,4]imidazole-4-pentanoic acid) and any biotin derivatives and analogs. Such compounds include, for example, biotin-e-N-lysine, biocytin hydrazide, amino or sulfhydryl derivatives of 2-iminobiotin and biotinyl-ε-aminocaproic acid-N-hydroxysuccinimide ester, sulfosuccinimideiminobiotin, biotinbromoacetylhydrazide, p-diazobenzoyl biocytin, 3-(N-maleimidopropionyl)biocytin and any covalent or non-covalent adduct of biotin with other moieties such as biomolecules, e.g. nucleic acids (including DNA, RNA, DNA/RNA chimeric molecules, nucleic acid analogs and peptide nucleic acids), proteins (including enzymes, peptides and antibodies), carbohydrates, lipids, etc. Such adducts of biotin with other moieties are also referred to herein as "biotinylated moieties".

The term "biotin-binding" compound as used herein is intended to encompass any compound which is capable of tightly but non-covalently binding to biotin or any biotin compound. Preferred biotin-binding compounds include streptavidin and avidin, as well as derivatives and analogs thereof, including streptavidin and avidin conjugated to other moieties, e.g. proteins.

It has been shown that the use of a substantially aqueous solution, preferably under the temperature conditions herein described, is effective to disrupt a complex comprising a biotin compound and a biotin-binding compound, e.g. a biotin-streptavidin (or avidin) linkage, without the need for more rigorous treatment, i.e. in the absence of additional processing steps. The exact mode of action of the aqueous solution on biotin decomplexation is not known. However, without wishing to be bound by theory, it is believed that the mechanism behind the reversible dissociation is due to a conformational change in the biotin-binding compound (e.g. a streptavidin-coated substrate) which results in release of the bound biotin (or biotinylated moiety). This theory is supported by the fact that the dissociation between the biotin-binding compound and biotin is completely reversed when salt is added.

Release or disruption or dissociation of the binding pair is conveniently effected by incubation in a substantially aqueous solution, preferably purified or distilled water. Purified water is especially preferred. Preferably, the purified water is obtained or obtainable by passing water, preferably distilled water, through an appropriate ion-exchange matrix or system, for example an appropriate Milli-Q matrix or system, which are commercially available and standard in the art. Especially preferably, distilled water is passed through a Milli-Q plus system using a Millipore Purification Pak, QPAK1 (Bedford, Mass., U.S.). The resulting water is generally at approximately 18.2M cm. Such methods of purifying water and equivalent methods are well known and standard in the art. Such purified water is also sometimes referred to as Milli-Q water or deionised water.

Incubation times will vary depending on the temperature used and may readily be determined by those skilled in the art for any given temperature conditions. Typically, incubation times will range up to 10 minutes, preferably up to 5 minutes, particularly preferably up to 2 minutes, e.g. up to 1 minute. Incubation times of up to 1 minute, e.g. about 1 second, have been found to be particularly effective in reversibly disrupting a biotin:biotin-binding compound linkage, e.g. a biotin-streptavidin linkage, at a temperature of about 80° C.

Typically, incubation will be effected at a temperature in the range of from about 20 to 95° C., preferably from 50 to 90° C., more preferably from 60 to 90° C. or 70 to 90° C., e.g. about 80° C. Particularly preferably, incubation will be accompanied by a gradual or stepped increase in temperature, e.g. a temperature gradient, to reach the desired temperature at which incubation is to take place. For example, the temperature increase may be stepped, e.g. by +1° C. every 2 seconds. Generally, in such methods using a temperature gradient, the temperature will be raised from ambient/room temperature, e.g. from around 20° C., to the desired incubation temperature.

Generally, in those cases in which the conjugate is incubated at elevated temperatures, the method of the invention will further comprise subsequent cooling (preferably to ambient temperature, e.g. to 25° C.) of the solution comprising the separated components. Rapid cooling will generally be preferred and may be effected by incubation on ice, preferably for up to 10 minutes, e.g. 1 to 5 minutes.

Aqueous solutions suitable for use in the invention will have water as the major component, i.e. at least 50% by volume being water, more preferably at least 60% or 70%, e.g. at least 806 or at least 90 or 95%. Such solutions will generally have a low content of dissolved solids (e.g. $Mg^{2+}$, $Ca^{2+}$, $Na^+$, $Li^+$ and monovalent and divalent ions in general, chlorides, sulfates, etc.). Preferably, these solutions will be purified using conventional purification techniques such as distillation or ion-exchange and will be substantially free from chemical impurities. Such chemical impurities may include, for example, amines and ammonium compounds. Preferably, the aqueous solution will be substantially free from ammonia or an amine, e.g. comprise less than 5% ammonia or amine, and more preferably less than 4%, 3%, 2% or 1% ammonia or amine. For example, the solution may be substantially free of $NH_3$ or any salt thereof or any ammonium ions, e.g. in the form of ammonium hydroxide and be substantially free of primary, secondary, tertiary or aromatic amines, or any compound of the formula $NR_3$ or $N^+R_4$ in which the R groups, which may be the same or different, are hydrogen, alkyl, cycloalkyl, alkenyl, alkynyl or aryl groups.

Purified or distilled water having a pH in the range 5 to 7, preferably 6.5 to 7, e.g. about 7, is generally preferred for use in the invention. Low ionic strength aqueous solutions are particularly preferred, e.g. pure water ($K_w = 10^{-14}$ at 25° C.).

Surprisingly, it has been found that the presence of chelating agents, in particular EDTA, in the incubating solution decreases the efficiency with which the biotin:biotin-binding compound linkage, e.g. the biotin-streptavidin (or avidin) linkage is cleaved. This is contrary to previous findings (Tong et al., Anal. Chem. 64:2672-2677, 1992). In a preferred embodiment of the invention the aqueous solution is thus substantially free from any chelating agent, e.g. EDTA and EGTA. Preferred aqueous solutions for use in the invention are those having a concentration of chelating agent (e.g. EDTA) less than 10 mM, preferably less than 5 mM. In a preferred embodiment of the invention the aqueous solution will contain no or only trace amounts of chelating agents. The presence of EDTA in even small amounts is particularly disadvantageous for methods of the invention where it is desired to carry out capillary sequencing on the dissociated products as it has been found to have an adverse affect on the injection phase into the capillaries used in certain types of sequencing machines (e.g. MegaBACE1 1000). Thus the presence of chelators, e.g. EDTA is generally to be avoided in such methods. Most preferably, the aqueous solution will be substantially free from any chelating agents such as EDTA.

Preferably, the aqueous solution for use in the invention will also be substantially free from any monovalent and divalent salts, e.g. sodium chloride, lithium chloride and magnesium chloride. For example, appropriate solutions will typically comprise less than 100 mM, preferably less than 50 mM, more preferably less than 25 mM, e.g. less than 10 mM NaCl. Preferred concentrations for LiCl lie in the same range, i.e. less than 100 mM, preferably less than 50 mM, more preferably less than 25 mM, e.g. less than 10 mM. Even relatively low concentrations of divalent salts such as $MgCl_2$ are found to result in a significant decrease in the efficiency of dissociation of the conjugate and these will typically be present in the release solution at a concentration of less than 10 mM. More preferably, the aqueous solution will be substantially free of divalent salts, e.g. $MgCl_2$.

Appropriate aqueous solutions and incubation times and temperatures to facilitate disruption of a conjugate between a biotin compound and a biotin-binding compound in the contacting step of the method can be readily determined by a person skilled in the art. Such solutions, times and temperatures are generally determined depending on the nature of the biotin compound or biotinylated moiety. An important advantage of the invention is that the conjugate can be disrupted under relatively mild conditions such that the structure of both the biotin compound and the biotin-binding compound remains intact. Thus, appropriate reaction conditions are selected in which both components of the conjugate are stable. For example, where the biotin compound is a biotinylated protein, vigourous conditions such as high temperature can denature the protein moiety and should be avoided. In other words, incubation conditions will generally be selected so as to avoid undesired destruction or denaturation of the biotin compound and/or the biotin-binding compound.

Typically, in the conjugate herein described, biotin will be bound or linked to one or more, preferably one, biological or chemical entity, e.g. a biomolecule. As explained above, such biotin compounds containing biotin linked to other entities are also referred to herein as "biotinylated moieties". Particularly preferably the biomolecule will be a nucleic acid molecule, a protein or a chimeric molecule, e.g. comprising both a nucleic acid and a protein component or indeed a chimeric molecule comprising component of any desired chemical nature, e.g. a protein (which term is used herein broadly to include any peptide or polypeptide), or a nucleic acid molecule coupled (or linked or bound in any way) to a small organic molecule, e.g. tag etc. The nucleic acid molecule may be any nucleotide sequence (whether a ribo- or deoxyribonucleotide sequence, i.e. DNA, RNA, or a mixture thereof, i.e. DNA/RNA, or any modification thereof), or any molecule which contains or incorporates a nucleotide sequence, e.g. a peptide nucleic acid (PNA) or any modification thereof. The nucleic acid molecule may be single or double stranded. The term "nucleic acid molecule" is thus considered to include constructs which may comprise a nucleic acid (nucleotide sequence) and another component, e.g. a protein, carbohydrate, radioactive or fluorescent marker, etc. Most preferably the biomolecule to which biotin is bound will be a DNA sequencing product or any primer extension product.

Examples of suitable proteins to which the biotin molecule may be coupled include antibodies, enzymes, binding proteins (e.g. combinatorial binding proteins), library or display products, peptides, etc.

Processes for coupling a biomolecule, e.g. a nucleic acid molecule or a protein molecule, to biotin (i.e. processes of biotinylation of molecules and entities) are well known in the art.

The biotin-binding compound, e.g. streptavidin (or avidin), may likewise be bound or linked to one or more (preferably one) biological, chemical or other entity. Thus, a conjugate suitable for use in the method of the invention may comprise any two moieties (e.g. biological or chemical moieties) linked by a streptavidin (or avidin)-biotin linkage.

In a preferred embodiment of the invention either the biotin or biotin-binding compound, e.g. streptavidin (avidin), is immobilised on an immobilising moiety, e.g. a solid support. Preferably, the biotin-binding compound, e.g. streptavidin (or avidin), will be immobilised on an immobilising moiety, e.g. a solid support. This may be any of the well-known supports or matrices which are currently widely used or proposed for immobilisation, separation, etc. in chemical or biochemical procedures. Thus, for example, these may take the form of particles, sheets, gels, filters, membranes, microfibre strips, tubes, wells or plates, fibres or capillaries, combs, pipette tips, microarrays or chips, and conveniently may be made of a polymeric material, e.g. agarose, cellulose, alginate, teflon, latex, plastic, polystyrene, glass or silica. Biochips may be used as solid supports to provide miniature experimental systems as described for example in Nilsson et al. (Anal. Biochem. 224:400-408, 1995) or as a diagnostic tool.

Preferred solid supports are materials presenting a high surface area for binding of the biotin or biotin-binding compund. Such supports will generally have an irregular surface and may for example be porous or particulate, e.g. particles, fibres, webs, sinters or sieves. Particulate materials e.g. beads are generally preferred due to their greater binding capacity, particularly polymeric beads/particles. Thus, particulate materials, especially beads, are generally preferred, a wide range of which are known in the art. Polymeric beads, for example Sepharose or polystyrene beads, may be used.

Conveniently, a particulate solid support used according to the invention will comprise spherical beads. The size of the beads is not critical, but they may for example be of the order of diameter of at least 1 and preferably at least 2 µm, and have a maximum diameter of preferably not more than 10 and more preferably not more than 6 µm. For example, beads of diameter about 2.8 µm have been shown to work well. To aid manipulation and separation of immobilized material, and also to facilitate automation if required, magnetisable ("magnetic") beads are preferred. Preferably such magnetic particles are superparamagnetic to avoid magnetic aggregation and clumping, and advantageously are monodisperse (i.e. are substantially uniform in size, e.g. size having a diameter standard deviation of less than 5%) to provide uniform kinetics and separation. The preparation of superparamagnetic monodisperse particles is described, for example, in EP-A-106873.

Streptavidin-coated magnetic beads sold as DYNABEADS by Dynal AS (Oslo, Norway) are particularly suitable for use in the invention.

Non-magnetic polymer beads suitable for use in the method of the invention are available from Dynal Particles AS (Lillestrøm, Norway) as well as from Qiagen, Amersham Pharmacia Biotech, Serotec, Seradyne, Merck, Nippon Paint, Chemagen, Promega, Prolabo, Polysciences, Agowa and Bangs Laboratories.

However, as indicated above, to aid manipulation and separation, magnetic beads are preferred. The term "magnetic" as used herein means that the support is capable of having a magnetic moment imparted to it when placed in a magnetic field, and thus is displaceable under the action of that field. Such supports are advantageous as they may readily be removed from other components of a sample by magnetic aggregation, which provides a quick, simple and efficient way of separating the particles following the binding of any biotin or biotinylated moieties. In addition, such magnetic aggregation is a far less rigorous method of separation than traditional techniques such as centrifugation which generate shear forces which may degrade any moieties, e.g. proteins or nucleic acids attached to the biotin molecules.

Thus, the magnetic particles with biotin or biotinylated moieties attached via conjugation to a biotin-binding compound, e.g. streptavidin (avidin), may be removed onto a suitable surface by application of a magnetic field, e.g. using a permanent magnet. It is usually sufficient to apply a magnet to the side of the vessel containing the sample mixture to aggregate the particles to the wall of the vessel and to remove the remainder of the sample so that the remaining sample and/or the particles are available for any desired further steps.

The surface of the solid support may be hydrophobic or hydrophilic, positively or negatively charged. Such surface properties may either be inherent in the material from which the solid support is made, e.g. supports made from polystyrene or other polymers or copolymers such as styrene/divinylbenzene are generally hydrophobic and silica supports are generally hydrophilic. Alternatively or additionally such surface properties may be achieved by coating the solid support with appropriate functional chemical groups or otherwise modifying the surface of the solid support to provide appropriate surface chemistry.

Generally, polystyrene surfaces or surfaces with some sulphate (—$SO_4$) surface groups display hydrophobic properties. Hydrophilic surfaces can however be imparted using one or more of a wide variety of functional surface groups, e.g. aldehyde (—CHO), aliphatic amine (—$CH_2CONH_2$), aromatic amine (-Φ —$NH_2$), carboxylic acid (—COOH), epoxy

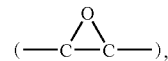

hydrazide (—CONH—$NH_2$), hydroxyl (—OH), sulphonate (—$SO_3$) and tosyl groups. Such functionalised surfaces can be prepared using techniques well known and documented in the art. For example, functionalised coated supports for use in the present invention may be prepared by modification of beads according to U.S. Pat. Nos. 4,336,173, 4,459,378 and 4,654,267.

Alternatively, supports with functionalised surfaces are commercially available from many manufacturers, such as those particle manufacturers described above. In particular hydrophobic beads are available from Dynal AS, Oslo, Norway, e.g. Dynabeads M-450 Epoxy (which have glycidyl ether (epoxy) groups on their surface), Dynabeads M-450 or M-280 Tosylactivated (which have p-toluene-sulphonyl (tosyl) groups on their surface) and Dynabeads M-500 Subcellular (which have p-toluene-sulphonyl (tosyl) groups on their surface). Hydrophilic beads are also available from Dynal AS, e.g. Dynabeads M-270 Epoxy (which have glycidyl ether (epoxy) groups on their surface), Dynabeads M-270 Carboxylic acid (which have carboxylic acid groups on their surface) and Dynabeads M-270 Amine (which have amino groups on their surface).

Particularly preferred solid supports for use in the present invention are hydrophilic or have a hydrophilic or substantially hydrophilic surface (e.g. Dynabeads M270), preferably a hydrophilic carboxylated surface and especially preferably are Dynabeads M-270 carboxylic acid.

The appropriate choice of surface may depend on the type of moieties which are attached to the biotin or the biotin-binding compound in the particular method concerned. For example, in embodiments of the invention where labelled hydrophobic terminator dyes are incorporated into the biomolecule moiety linked to the biotin molecule, e.g. in methods to carry out nucleic acid sequencing such as that described in Example 1, a hydrophilic surface is preferred to ensure as little non-specific binding as possible of the support to unincorporated hydrophobic terminator dyes.

Streptavidin (or avidin) (or any other biotin-binding compound), or biotin, if desired, may be attached to an immobilizing support by methods well known in the art. These include, for example, attachment through hydroxyl, carboxyl, aldehyde or amino groups which may be provided by treating the immobilizing support to provide suitable surface coatings.

In a convenient embodiment, the biotin-binding compound, e.g. streptavidin (or avidin), is attached to the support prior to contact with the sample containing biotin or biotinylated moieties. Again, appropriate supports to which streptavidin (or avidin) has already been attached are commercially available. A preferred support for use in the invention is Dynabeads M-270 Streptavidin which is available from Dynal AS, Oslo, Norway. Alternatively, the biotin-binding compound, e.g. streptavidin (or avidin), may be attached to the support after the conjugate with biotin has been formed.

Once the biotin:biotin-binding compound complex has been disrupted, the biotin-binding compound may be re-used, e.g. following re-conditioning using a salt solution such as NaCl or LiCl. For example, following cleavage of biotin (or a biotinylated moiety) from a streptavidin/avidin support, the support may be re-conditioned using techniques known in the art, e.g. by washing with a binding buffer such as 1M or 2M NaCl or LiCl which may optionally be used in combination with TE (10 mM Tris pH 7.5, 1 mM EDTA). Methods which involve such an additional re-conditioning step form a preferred embodiment of the invention. After re-conditioning, the biotin-binding compound (e.g. the streptavidin/avidin solid supports) may be re-used in a further method to attach biotin or biotinylated moieties. Preferably, such reconditioned supports are re-used in a further method of the invention wherein any conjugate comprising biotin or biotinylated molecules and a biotin-binding compound formed on the support can be disrupted by incubation with an effective amount of a substantially aqueous solution as described herein.

Other additional and optional steps for use in conjunction with the methods described herein will be readily apparent to a person skilled in the art and can readily be determined depending on the nature of the experiment. For example, once the conjugate between the biotin-binding compound and biotin has formed on a solid support, the solid support may be subjected to one or more washing steps, e.g. to remove any undesired impurities, e.g. non-bound reactants. Once formed, the conjugate on the solid support may be subjected to any appropriate manipulation steps, for example, in the cases where nucleic acid molecules are present, primer binding and the performing of amplification reactions or sequencing reactions can take place according to any suitable method. Appropriate exemplary methods will be discussed in more detail below.

In addition, as will be described in more detail below, in preferred embodiments after the disruption of the conjugate between the biotin-binding compound and biotin, the biotin or biotinylated moiety may be purified or isolated using any appropriate method, or subjected to further manipulation or analysis. Indeed, the use of the methods of the invention to isolate and/or purify biotin or biotinylated moieties form a preferred embodiment of the invention. For example, biotinylated moieties can readily be separated from non-biotinylated moieties simply by contacting a reaction mixture with immobilized biotin-binding compound, e.g. covalently bound to a solid support, followed by separation and washing of the immobilized complex of the biotin compound with the biotin-binding compound. The biotinylated moieties can then be isolated by dissociation of the biotin:biotin-binding compound complex using the methods of the invention described herein. It will of course be appreciated that a biotin-binding compound can be purified by an analogous process, e.g. by contacting a reaction mixture containing a biotin-binding compound with an immobilized biotin compound to form a complex, followed by purification and subsequent dissociation of the complex.

Depending on the desired use of the conjugate herein described, one or more of the biotin-binding compound, e.g. streptavidin (or avidin), or a moiety attached to the biotin-binding compound, or the biotin compound or the biotinylated moiety, may be provided with a label or indeed any reporter molecule. This may be any label known in the art or described in the literature, e.g. a radioactive label, an enzyme marker, or some other detectable label, e.g. a coloured, pigmented, chromogenic, fluorescent or chemiluminescent label. Also included as "labels" are any "signalling" moieties which may contribute to a detectable reaction, e.g. a substrate for an enzyme, reaction component, etc.

The method herein described may be used for any application in which disruption of binding and preferably reversible binding of biotin (or a biotinylated moiety) and a biotin-binding compound such as streptavidin (or avidin) is desirable. For example, this may be used in methods for the detection, identification, determination, purification, separation and/or isolation of target protein or nucleic acid molecules, e.g. target biotinylated moieties such as biotinylated DNA. Other methods include the production, e.g. copying or replication or amplification, of a target nucleic acid molecule, e.g. a target biotinylated nucleic acid molecule. Preferably in such uses, following release of the binding pair, i.e. following release of the biotin or biotinylated moiety, the streptavidin support may be re-used.

The method of the invention may, for example, be used in any conventional separation, purification or isolation technique, in particular those which have been adapted for use on a solid support. Such techniques include immunoassays (e.g. immunoseparation assays), DNA-based assays, sequencing, in vitro amplifications, etc. A preferred use of the method is in a procedure for the regeneration of probes for DNA arrays. Purification procedures in which the method may be used include those conventionally used to separate cells, nucleic acids, proteins and other biomaterials, organic compounds, etc., for example procedures used in high throughput drug screening.

The method of the invention has particular utility in PCR and analogous nucleic acid amplification techniques, or indeed in any procedure involving an in vitro amplification or chain extension step (i.e. a template-directed polymerase catalysed primer extension reaction, including those in which the polymerase is a reverse transcriptase). For example, the biotin-streptavidin interaction may be used in solid phase sequencing techniques which involve binding of biotinylated ssDNA sequencing products, or dsDNA, onto streptavidin-coated magnetic beads followed by, for example, elution of the non-biotinylated strand, e.g. using NaOH. Using the method of the invention biotinylated DNA sequencing products may be bound onto and subsequently released from streptavidin-coated beads in a reversible manner. The beads can then be re-used (after for example subjecting the beads to a reconditioning step as described above) to capture a new set of biotinylated cycle sequencing products. Single stranded biotinylated sequencing products may equally be bound onto and subsequently released from streptavidin beads using the methods of the invention. In such methods the elution of the non-biotinylated strand is not required and the biotinylated sequencing products can simply be released using the methods of the invention and analysed, e.g. with a sequencing machine. A general schematic of such a technique is described in FIG. 1 and the Examples. As the method of the invention can be used in sequencing techniques, it can be used in the identification or determination of nucleic acid molecules.

In addition, the methods of the invention can be used to purify or isolate desired biotinylated products such as desired biotinylated proteins or nucleic acid molecules. In particular, the methods can be used to purify or isolate biotinylated PCR products in a single or double stranded form. For example, PCR amplification of a desired target nucleic acid sequence can be carried out on a sample using one or more biotinylated primers in accordance with methods well known and documented in the art. These biotinylated PCR products can then be attached to a streptavidin (avidin) solid support, separated from the remainder of the sample using an appropriate method (e.g. magnetic separation) after which they can be released from the support using the methods of the invention and analysed or subjected to further manipulation steps. Optionally, if desired, the desired PCR products can be attached to the solid supports and rendered single stranded by eluting off the non-biotinylated strand, after which the single stranded products can be eluted and analysed or eluted and subjected to further downstream manipulation steps such as further amplification steps. If appropriate, such further manipulation steps can equally be carried out while the single stranded product is attached to the solid support, after which the final products can then be eluted using the methods of the invention. General schematics of examples of such techniques are shown in FIGS. 25 and 26. In all these techniques the solid supports are advantageously reused as described above in order to increase the amount of product purified, or for example to isolate a different/distinct product.

Viewed from a further aspect the invention thus provides a method of releasing a biotinylated moiety, preferably a biotinylated molecule or cell (e.g. biotinylated DNA), from a support comprising a biotin-binding compound, e.g. a streptavidin or avidin support, said method comprising the step of eluting said support with a substantially aqueous solution, preferably at a temperature in the range of from about 20 to 95° C., more preferably from 50 to 90° C., particularly preferably from 60 to 90° C. or 70 to 90° C., e.g. about 80° C., whereby to effect release, preferably reversible release of said moiety.

Viewed from a yet further aspect the invention provides a method of reversibly immobilising a biotinylated moiety, preferably a biotinylated molecule or cell (e.g. biotinylated DNA), said method comprising the following steps:

(a) binding said biotinylated moiety to a support comprising a biotin-binding compound, e.g. a streptavidin or avidin support; and subsequently (b) eluting said support with a substantially aqueous solution, preferably at a temperature in the range of from about 20 to 95° C., more preferably from 50 to 90° C., yet more preferably from 60 to 90° C. or 70 to 90° C., e.g. about 80° C., whereby to effect release, preferably reversible release, of said biotinylated moiety. In such methods, once released the biotinylated moieties may be subjected to further manipulation or analysis using appropriate techniques.

In a yet still further aspect the invention provides the use of any method as herein described in a nucleic acid amplification technique, preferably in a method of amplification of DNA, or in a nucleic acid sequencing technique, e.g. cycle sequencing with dye terminators.

The milder elution conditions used in the method of the invention provide two major advantages over the harsh conditions conventionally used. Firstly, the release is reversible, which means that both the biotin-binding compound (e.g. streptavidin) and biotin can be reused. For example, following elution the streptavidin-coated beads can be reused to capture a new set of biotinylated molecules, e.g. biotinylated cycle sequencing products or biotinylated amplified PCR products. Since the biotin molecule also remains intact after release, the biotinylated molecules can also be bound to a new set of beads and released a second time. The possibility to elute biotinylated molecules at relatively mild conditions from the streptavidin support and re-use both the biotin and the streptavidin opens new possibilities for future applications. Furthermore, the ability to re-use the streptavidin support significantly reduces the cost of existing assays, e.g. in automated DNA sequencing assays.

Secondly, molecules or cells previously considered too fragile to withstand the harsh conditions currently used to break the biotin-streptavidin bond can be successfully eluted from a biotin-binding compound, e.g. a streptavidin support and if desired subjected to downstream manipulation or analysis. This opens up the possibility of new avenues and developments of novel methods in a wide variety of fields.

Although the method of the invention is primarily described in relation to a conjugate comprising a biotin-streptavidin or biotin-avidin linkage, it will be generally understood that this may extend to disruption of any conjugate comprising any known derivative of biotin, streptavidin or avidin capable of forming an affinity binding pair. Biotin may, for example, be modified by binding to other biological or chemical entities without significantly disrupting its ability to bind to a streptavidin (or avidin) support.

Streptavidin is commercially available in a number of different forms, including mutated as well as native forms, each of which may be used in the invention. Both native and recombinant forms of streptavidin and avidin (in the form of tetramers, dimers, monomers, or any combination thereof) may be used in the methods herein described. Indeed, it is anticipated that any fragment or modified form of streptavidin or avidin which is capable of binding to biotin may be used. For example, streptavidin (or avidin) may be bound to any other biological or chemical entity which does not significantly affect its ability to bind to biotin.

In its broadest aspect the invention thus provides a method of disrupting a conjugate comprising at least one biotin molecule or derivative thereof linked to at least one biotin-binding compound or derivative thereof (e.g. to a streptavidin or avidin molecule or derivative thereof), said method comprising the step of contacting (e.g. incubating) said conjugate with a substantially aqueous solution whereby to disrupt, preferably reversibly disrupt, said conjugate. Preferably, the method will be effected at a temperature in the range of from about 20 to 95° C., more preferably from 50 to 90° C., yet more preferably from 60 to 90° C. or 70 to 90° C., e.g. about 80° C.

DETAILED DESCRIPTION OF THE FIGURES

The invention will now be described in more detail in the following non-limiting Example and with reference to the accompanying figures.

Figure 4:
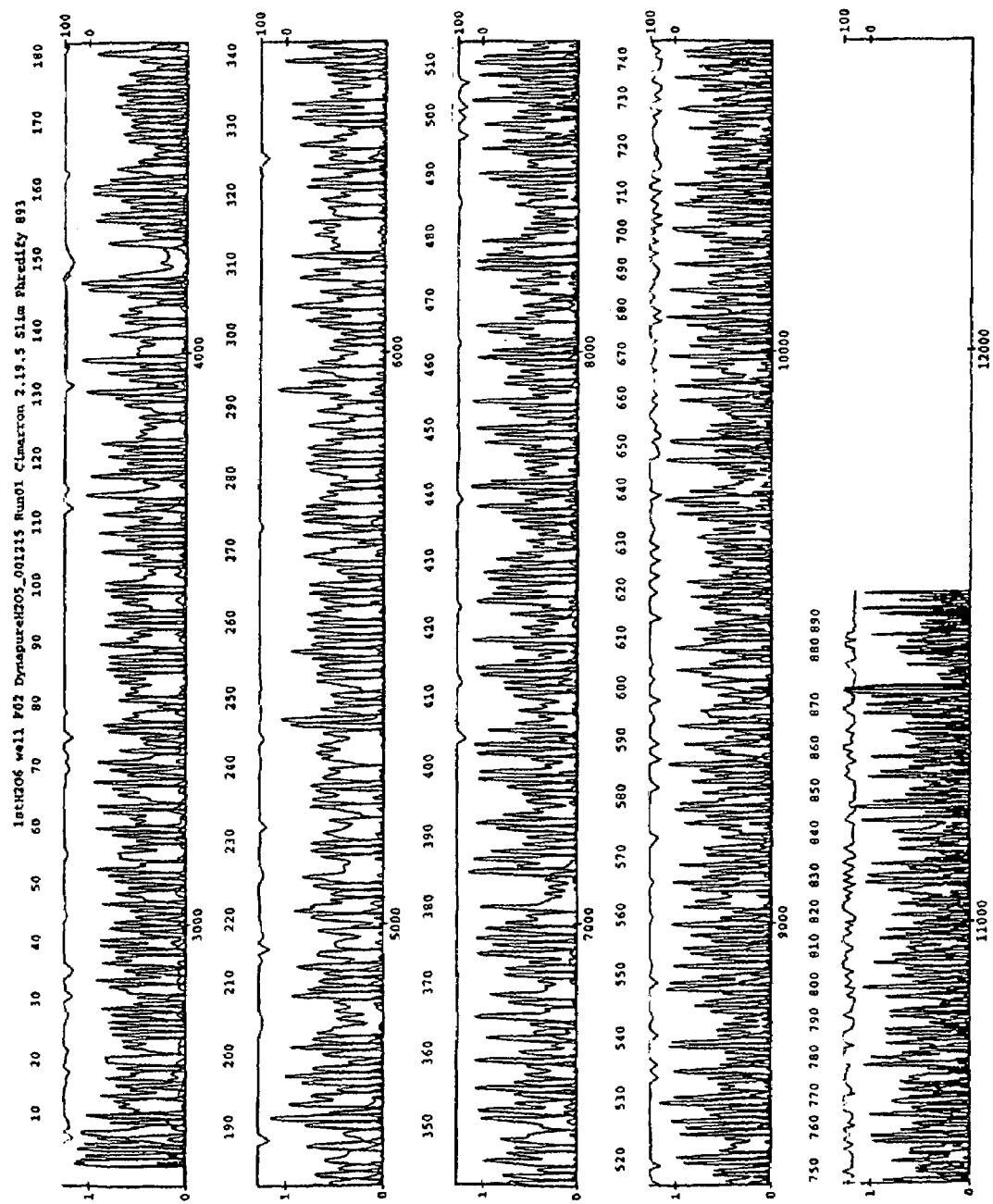
Figure 5:
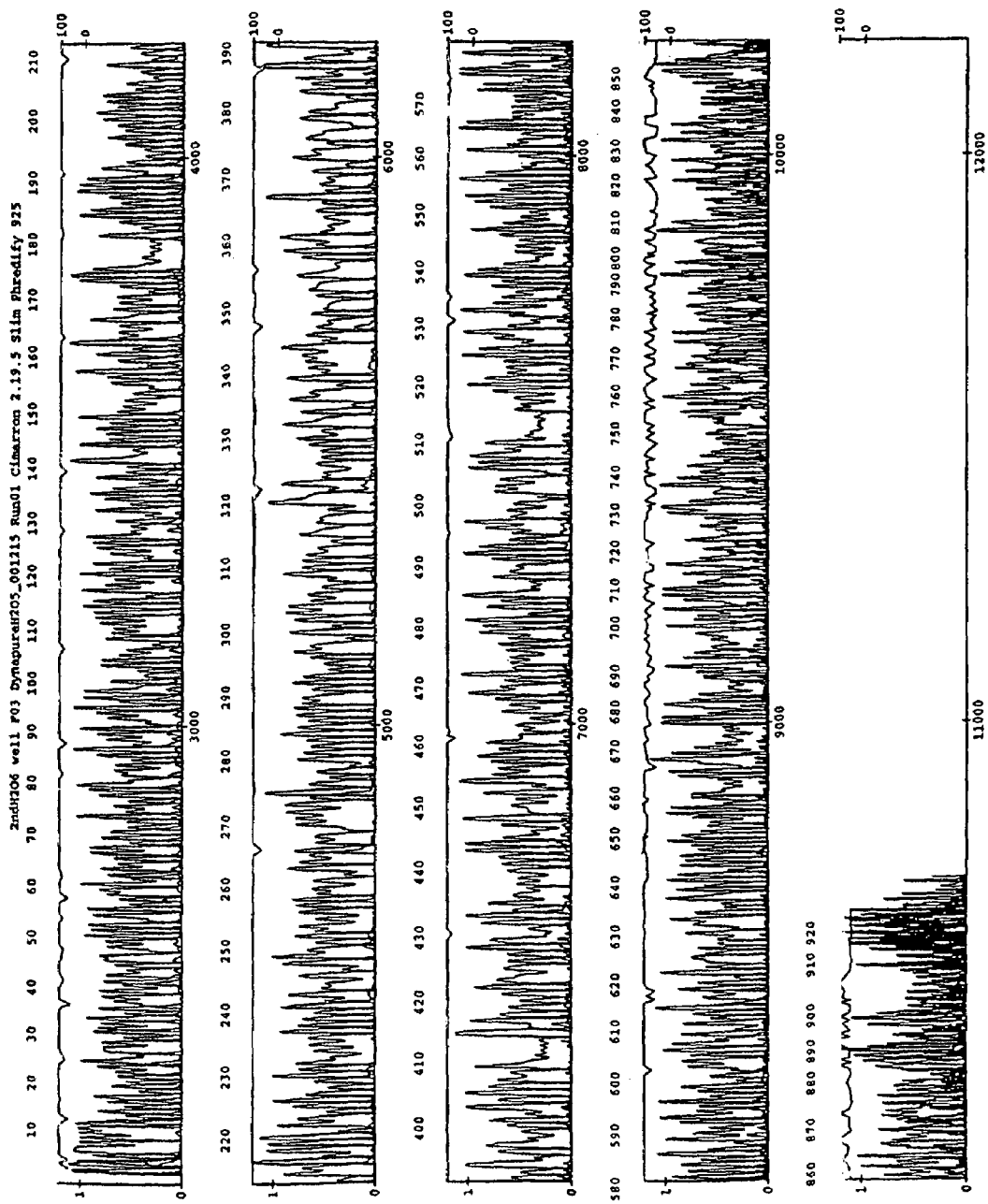
Figure 6:
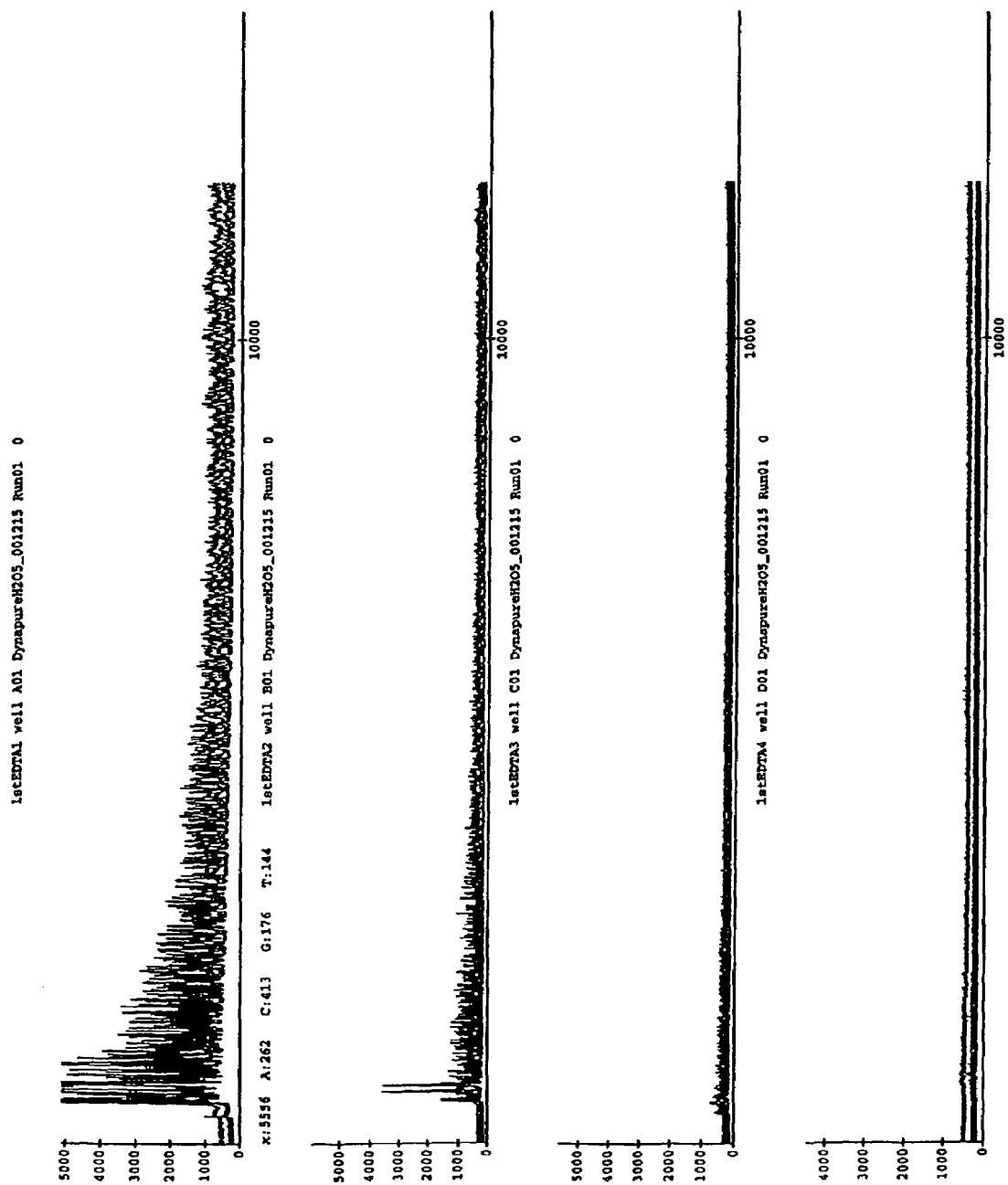
Figure 7:
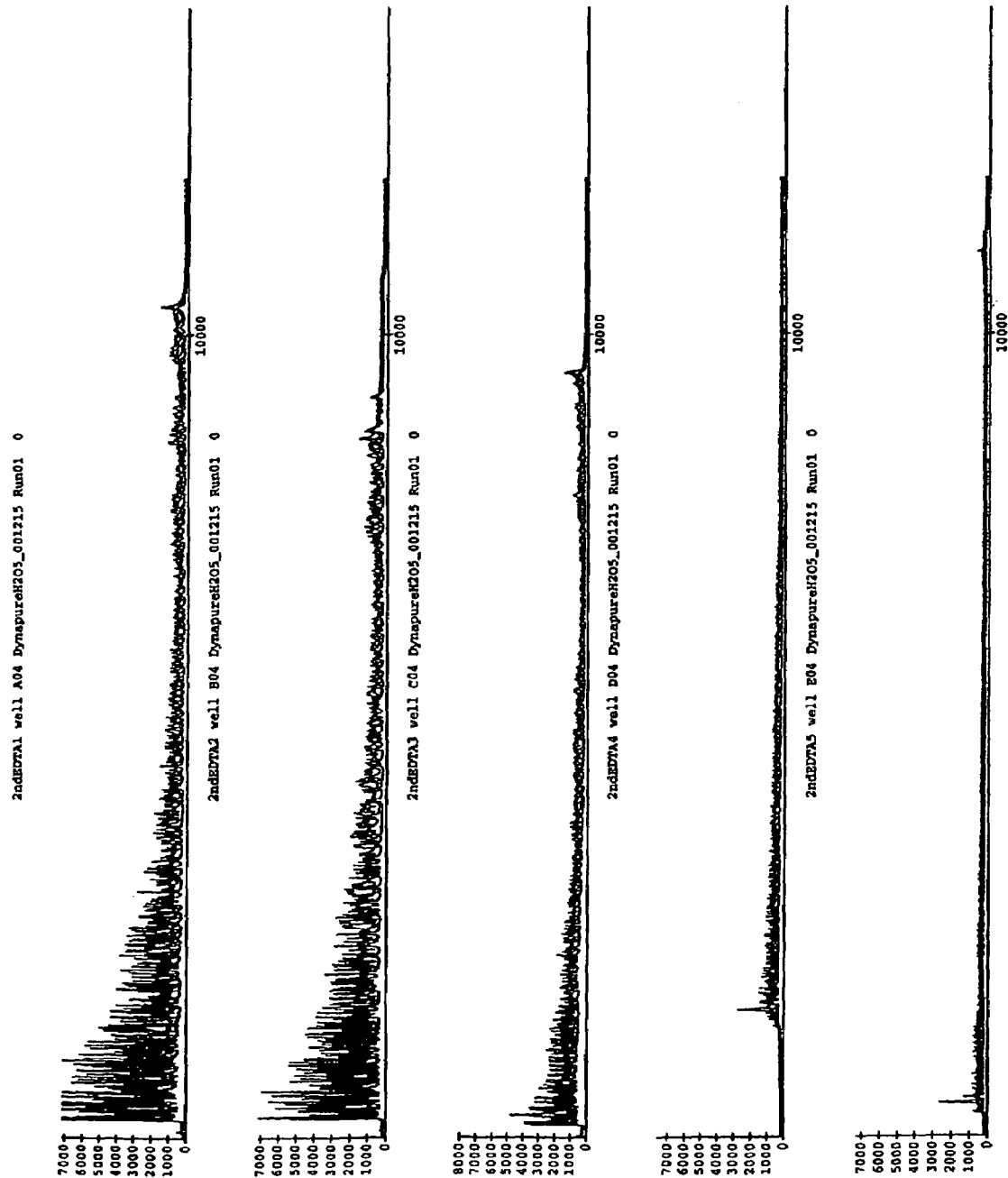
Figure 8:
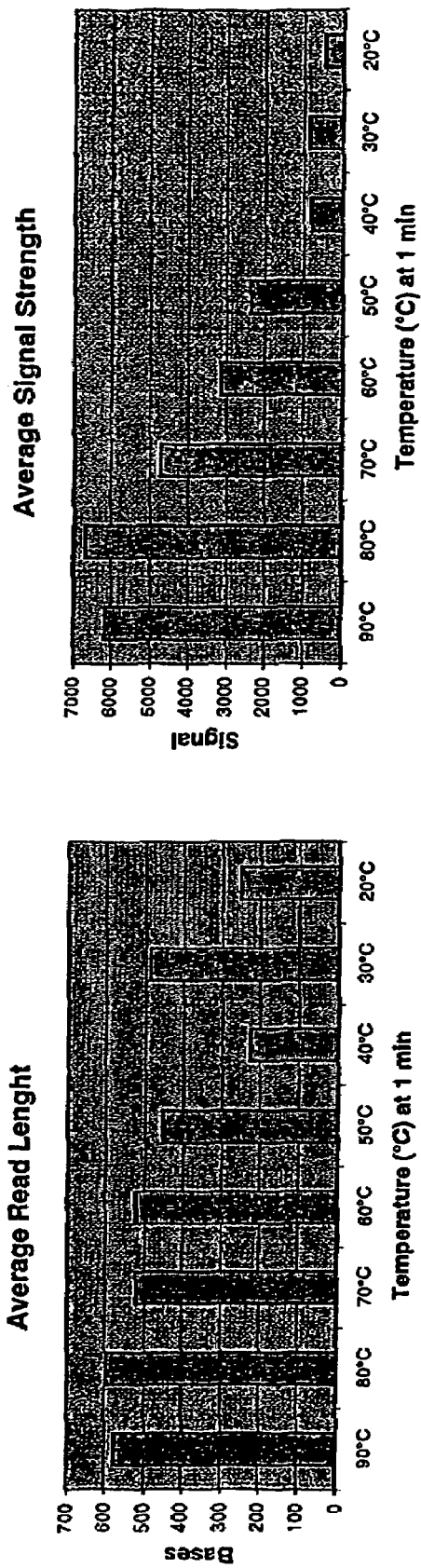
Figure 9:
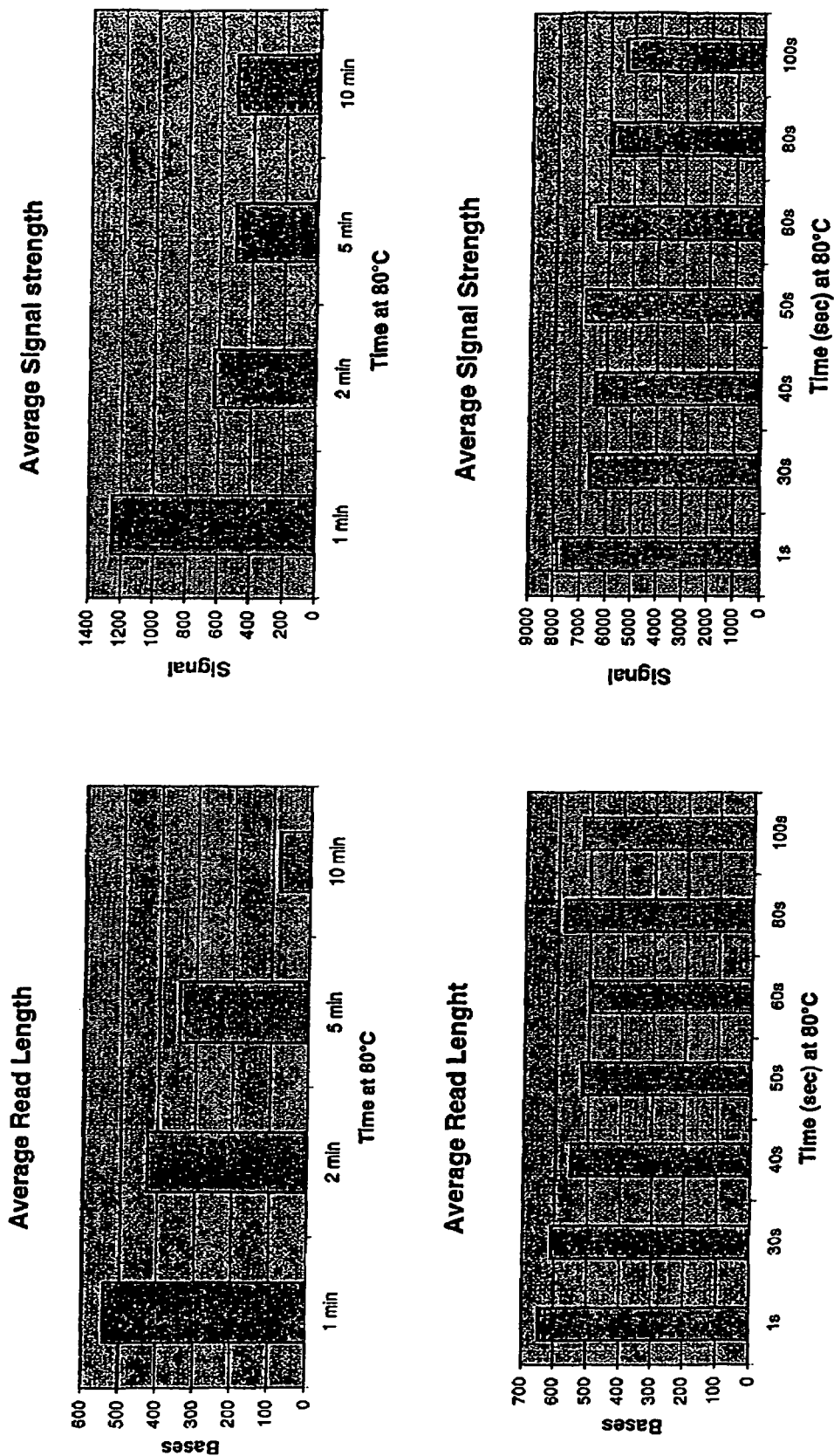
Figure 10A:
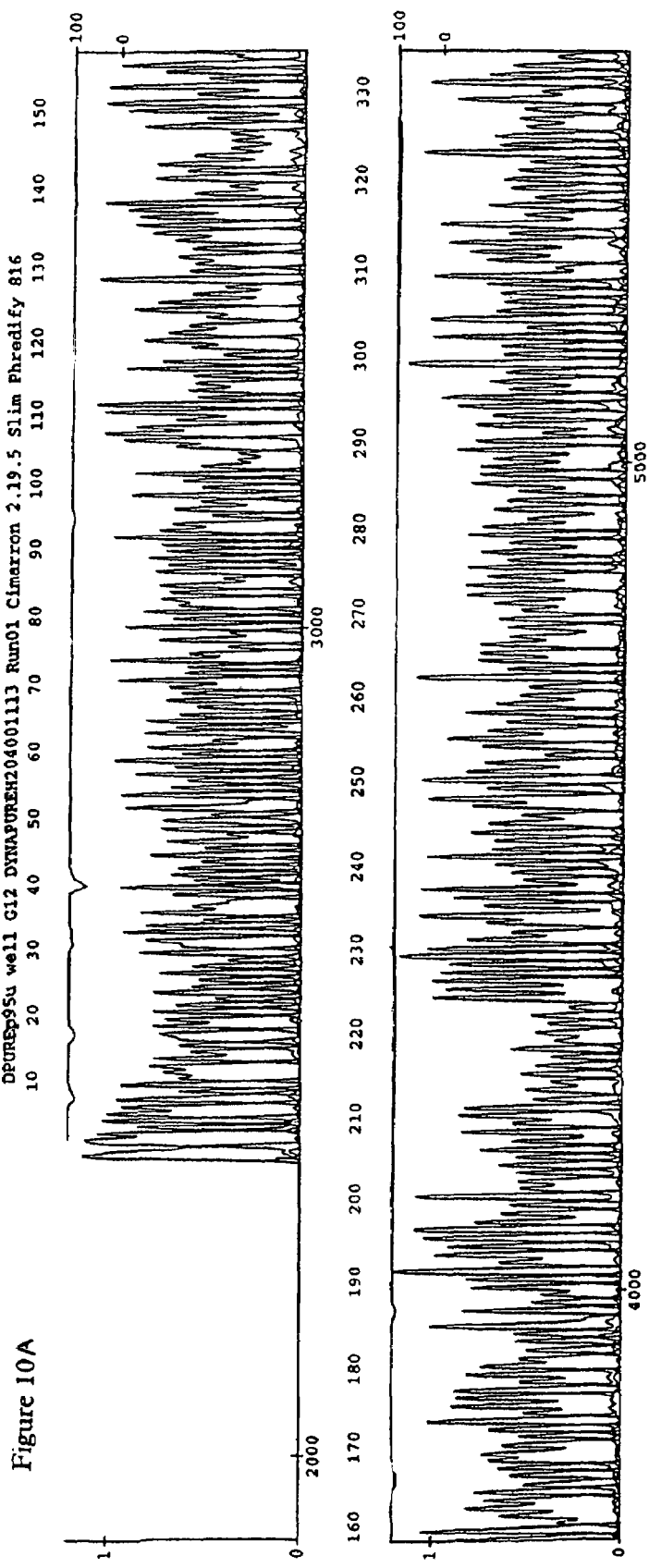
Figure 10B:
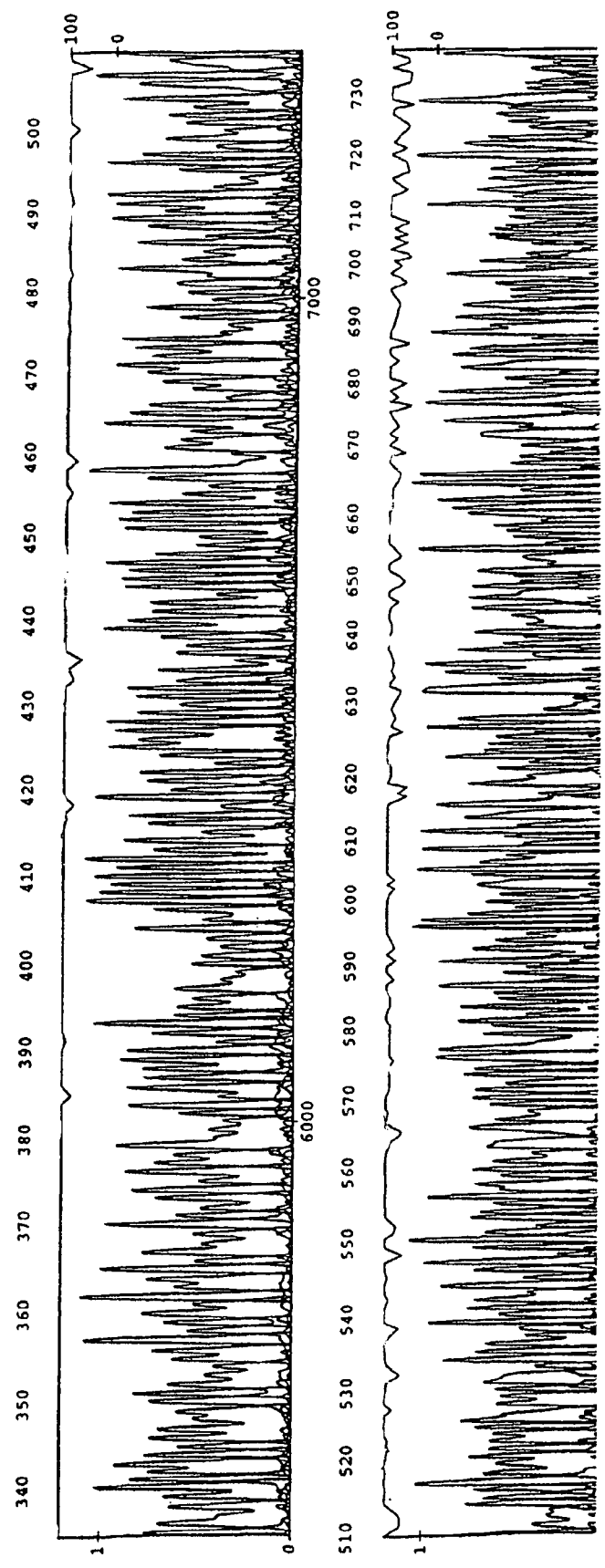
Figure 19:
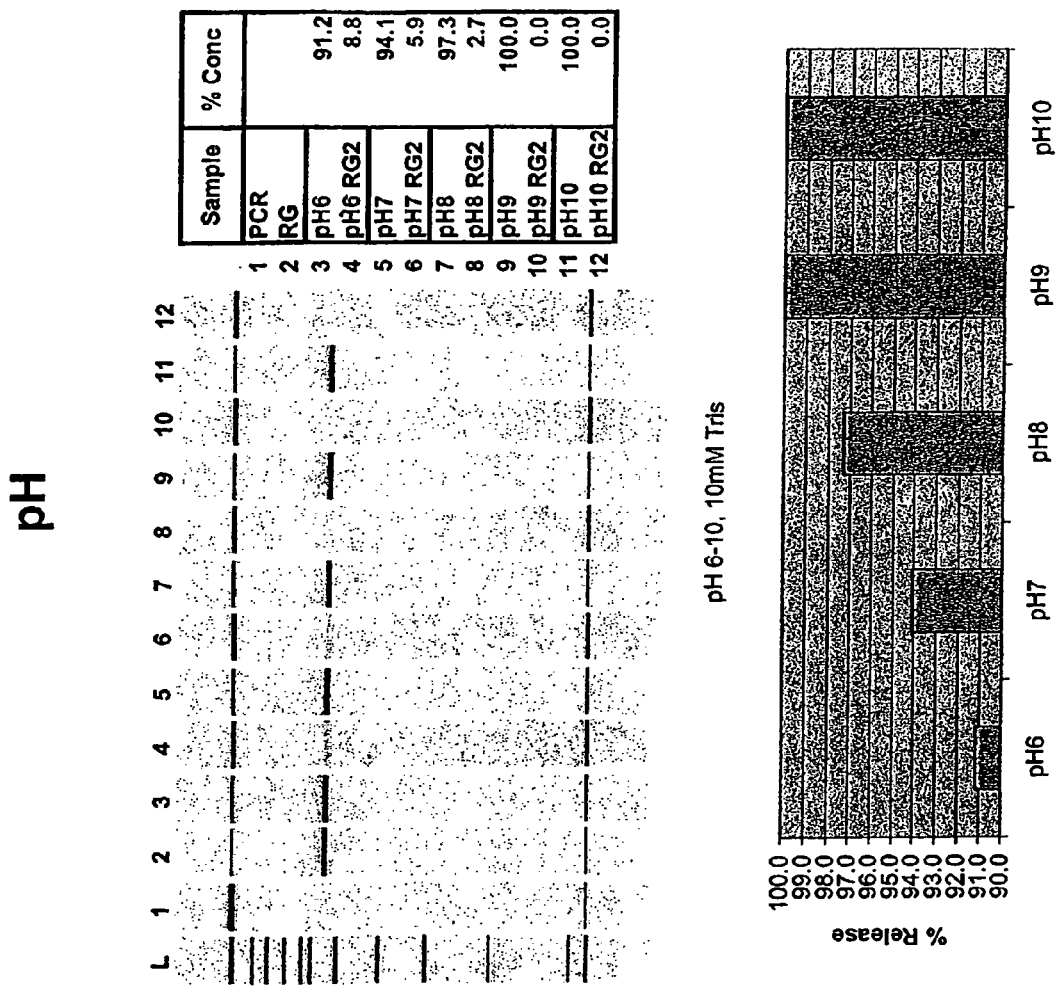
Figure 20:
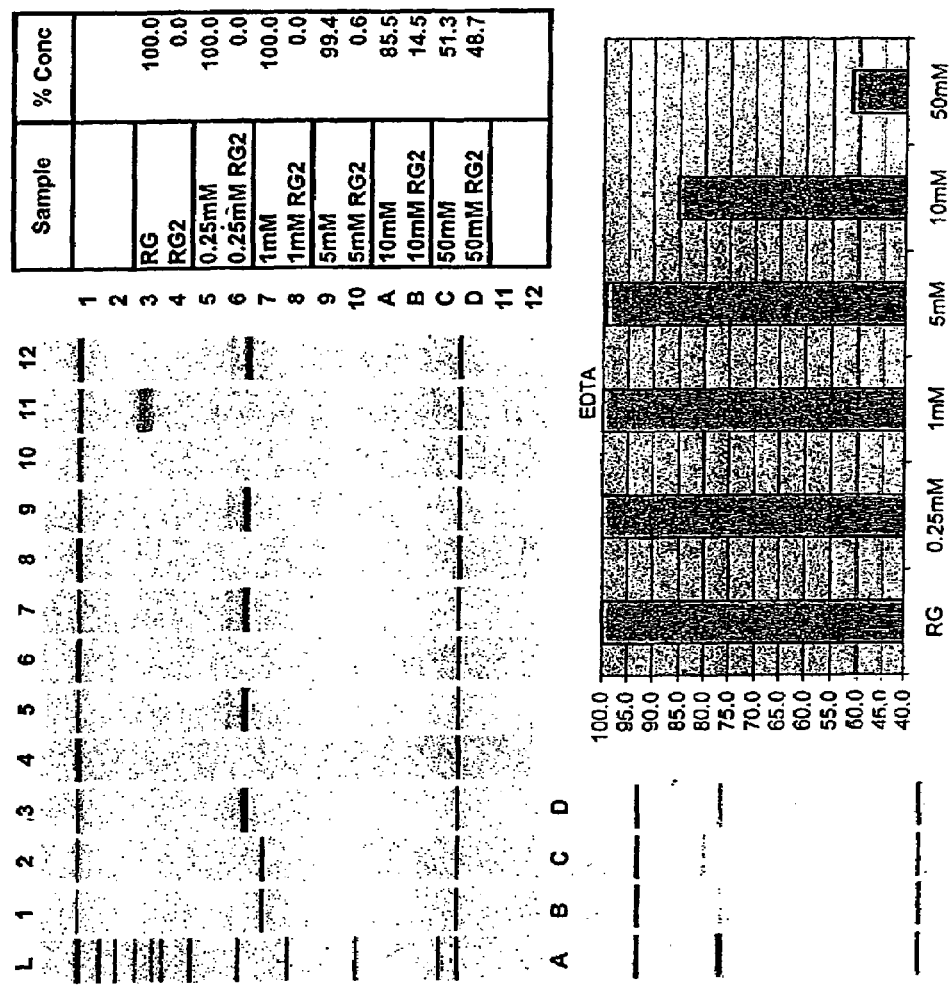
Figure 21:
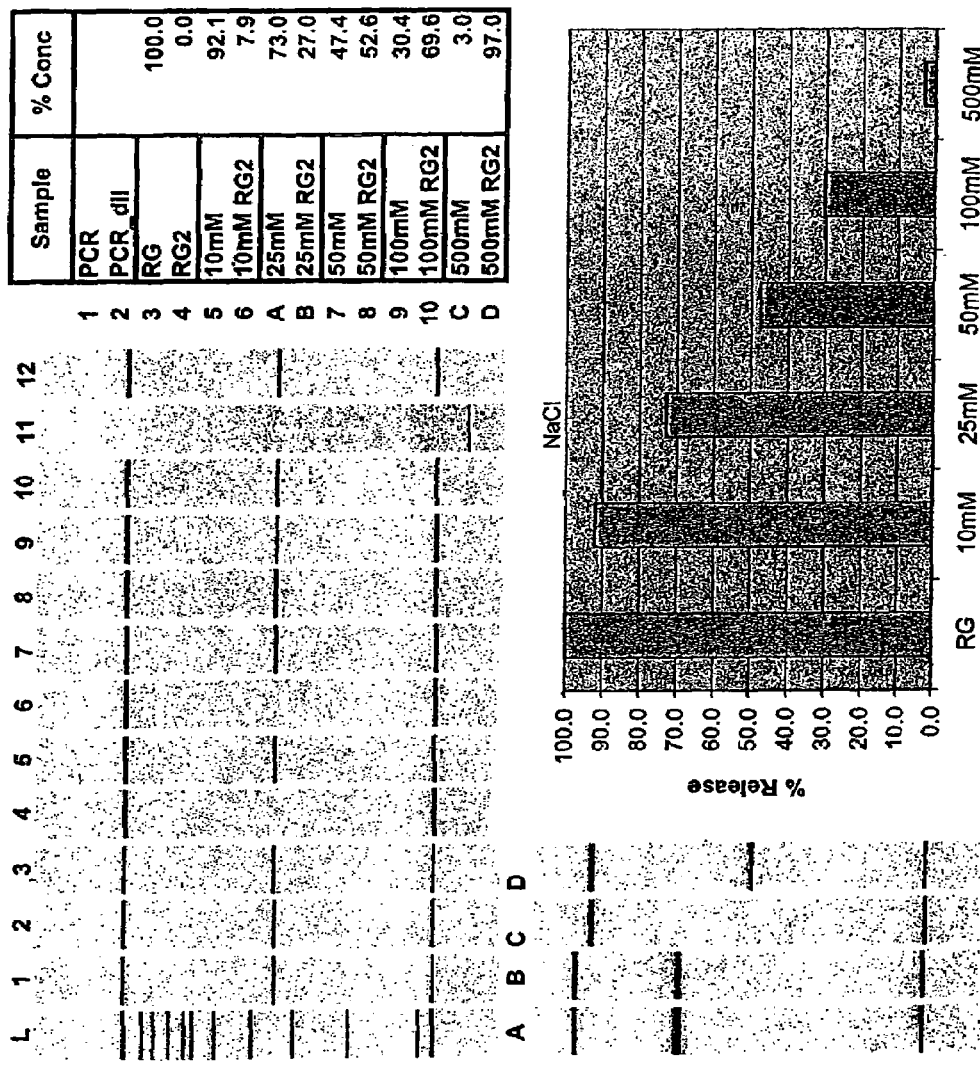
Figure 22:
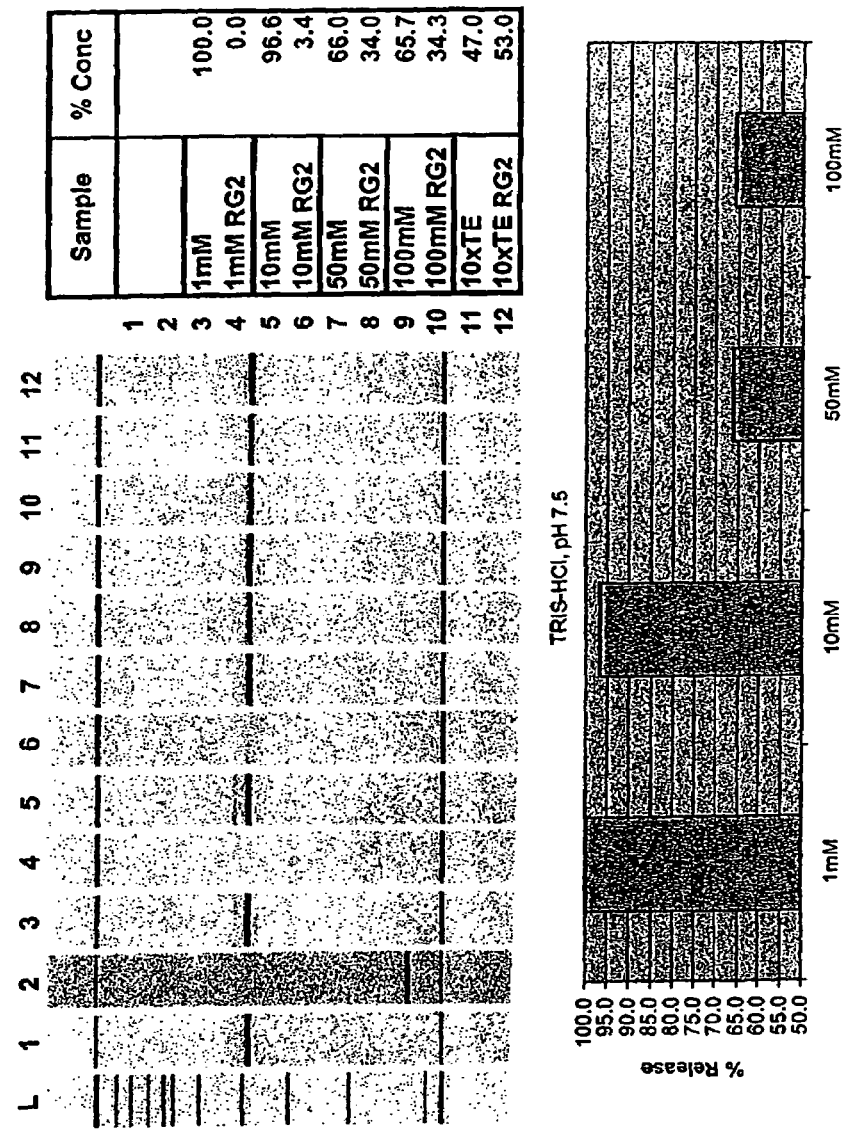
Figure 23:
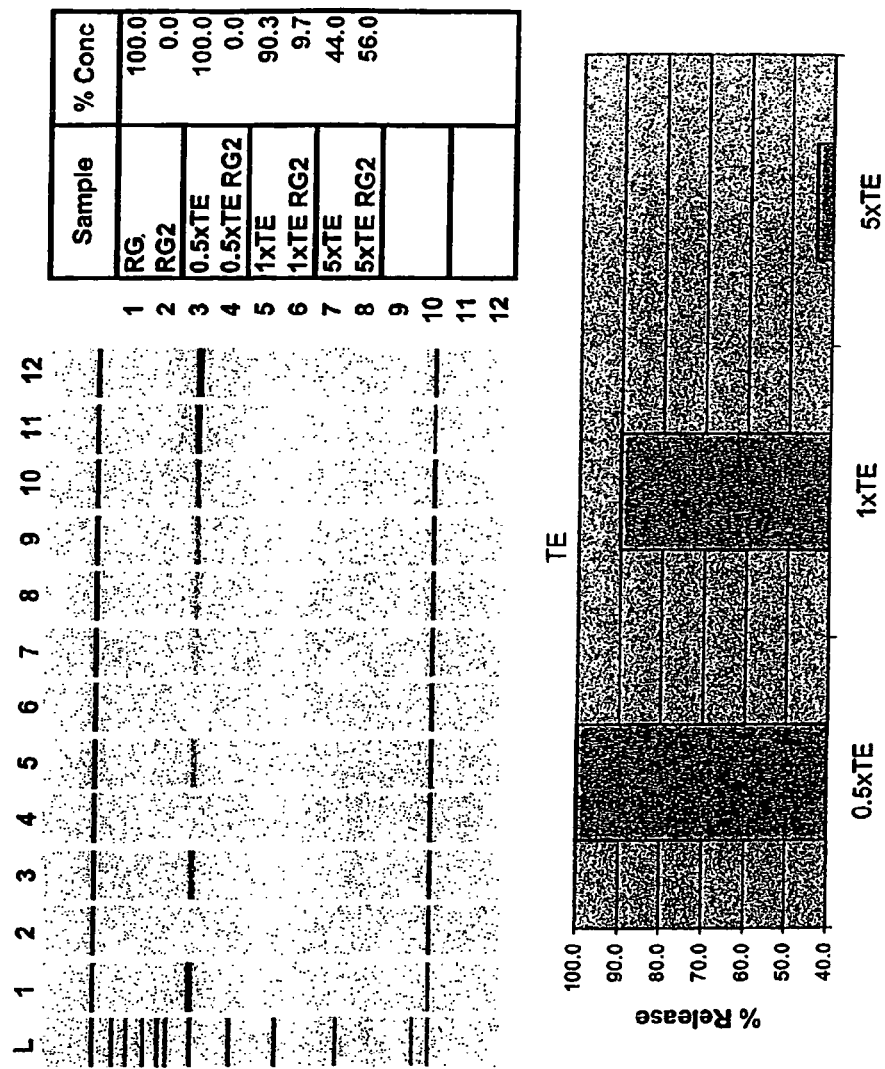

FIGS. 4 and 5 respectively demonstrate the non-denaturing of biotin following release. FIG. 5 shows the results after a second capture of released biotin;

FIG. 6 shows the raw data from samples released in EDTA directly loaded on the MegaBACE1000. From top to bottom: [Water, 0.25 mM, 0.5 mM, 1 mM EDTA];

FIG. 7 shows the raw data from samples first released in EDTA, again captured, this time released in water and directly loaded on the MegaBACE1000. From top to bottom: [Water, 0.25 mM, 0.5 mM, 1 mM EDTA];

FIG. 8 shows the temperature dependence of the release at 1 min incubation;

FIG. 9 shows the incubation time dependence of the release at 80° C.;

FIG. 10A and 10B show a sequence run result after six times re-use of streptavidin beads;

FIGS. 11-18 show the incubation time and temperature dependence of the release in pure water;

FIG. 19 shows the pH dependence of the release;

FIG. 20 shows the effect of EDTA concentration on the release;

FIG. 21 shows the effect of the NaCl concentration on the release;

FIG. 22 shows effect of concentration of Tris buffer on the release;

FIG. 23 shows the effect of concentration of TE buffer on the release; and

Figure 24:
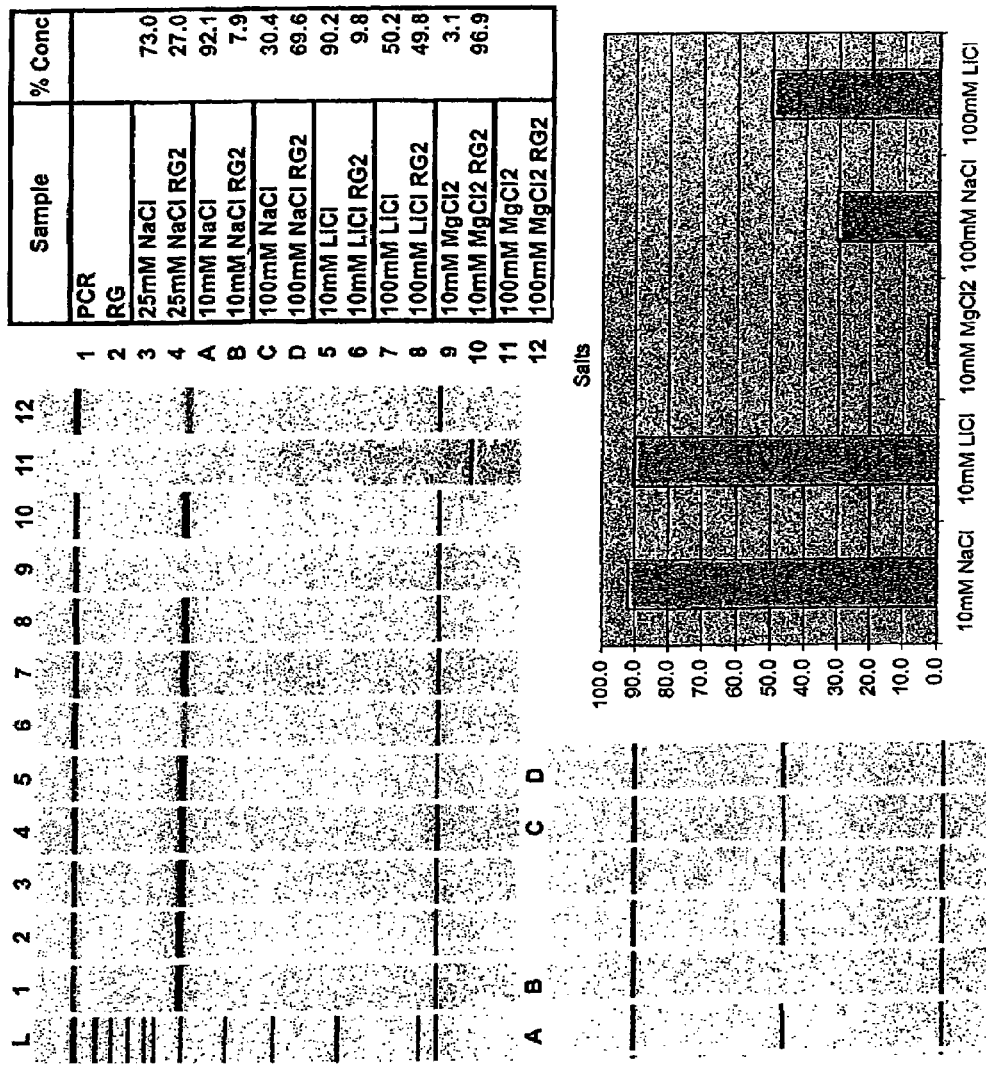

FIG. 24 shows the effect of concentration of various salts on the release.

Figure 25:
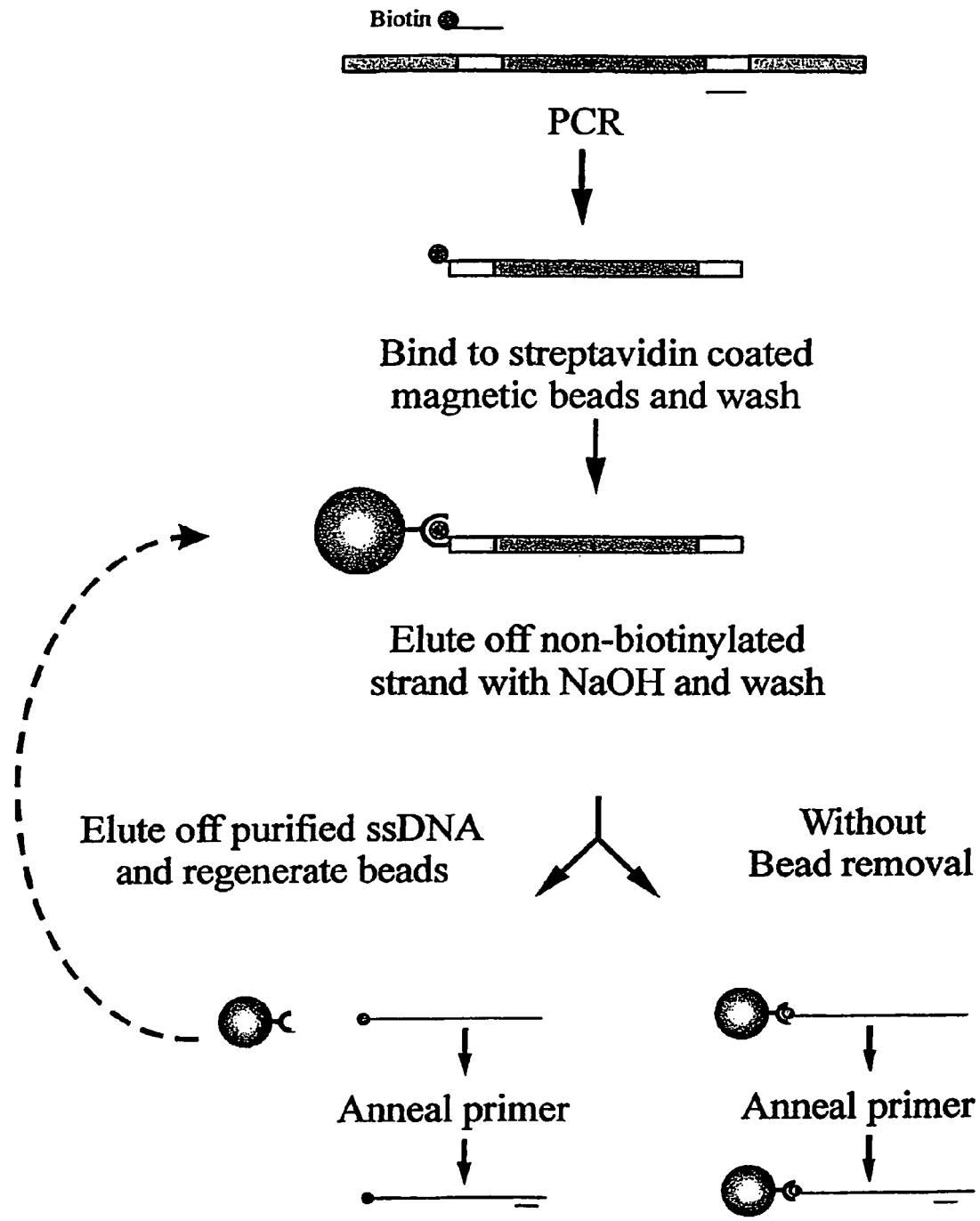

FIGS. 25 and 26 are schematic drawings illustrating how the methods of the invention may be used.

EXAMPLE 1

1.1 Materials and Methods

Preparation of DNA from Shot-Gun Genomic Libraries

The method described here used DNA derived from colonies in a genomic shotgun library sub-cloned in pCR4-BLUNT™ (Invitrogen). The colonies were picked into 100 µl 1×TE (10 mM Tris-HCl (pH 7.5), 1 mM EDTA) and subsequently lysed by heating for 40 seconds in a microwave oven. 10 µl of the lysate were directly used as template for a 50 µl PCR reaction.

Preparation of PCR-Products

10 µl of the lysates were used as templates in 50 µl PCR reactions with RIT 27 (5'-GCTTCCGGCTCGTATGTTGT-GTG-3') (SEQ ID NO. 1) and RIT 28 (5'-AAAGGGGGAT-GTGCTGCAAGGCG-3')(SEQ ID NO. 2) primers. Amplification conditions used were 10 mM Tris-HCl (pH 8.3), 50 mM KCl, 2 mM MgCl, 0.1% Tween 20, 0.2 mM of each dNTP, 0.5 U of AmpliTaq DNA polymerase (Perkin-Elmer, Norwalk, Conn., USA) and 75 nM of each primer using a PTC 225 thermocycler (MJ Research, Waltham, Mass., USA). The temperature profile used was 95° C. for 5 minutes, followed by 35 cycles at 96° C. for 15 seconds, 65° C. for 30 seconds, and 72° C. for 2 minutes, ending with 72° C. for 10 minutes.

Cycle Sequencing with Dye Terminators

Dye terminator cycle sequencing reactions were performed with the DYEnamic™ ET terminator cycle sequencing kit (available from Amersham Pharmacia Biotech, Piscattaway, N.J., USA) in the following way: 5 pmol of the biotinylated M13 (−28) (5'-CACACAGGAAACAGCTAT-GAC-3')(SEQ ID NO. 3) reverse sequencing primer were used together with 8 µl sequencing reaction pre-mix and 1.5 µl crude PCR product in a total volume of 20 µl.

Capture and Elution of Biotinylated Cycle Sequencing Products

For each reaction, 70 µg of M270 Streptavidin beads (Dynal AS, Oslo, Norway) were used. The beads were initially washed once to remove storage buffer and resuspended in 20 µl B/W buffer (10 mM Tris-HCl (pH 7.5), 1 mM EDTA, 2M NaCl, 0.1% Tween 20) and transferred to the cycle sequencing reactions. After 15 minutes incubation at ambient temperature with two intermittent mixes, the beads with bound DNA were magnetically collected and rinsed twice with 45 µl 70% ethanol to remove unincorporated dye terminators, salts, nucleotides PCR template and enzyme. Following the wash cycle, the beads with DNA still bound were resuspended in 20 µl distilled water and transferred to a new plate in a heating/cooling station. Finally, the biotin-streptavidin bond was released by heating the resuspension to 80° C., followed by cooling to ambient temperature. The beads were magnetically separated and removed from the solution, resulting in a clear reaction liquid in the plate. The beads were then transferred to the original bead tube and finally re-suspended in 7 µl 1×TE buffer (10 mM Tris-HCl (pH 7.5), 1 mM EDTA) and were ready for re-use in a new round without any further washes.

Evaluation using MegaBACE 1000 DNA Sequencer

The released DNA was directly ready for injection on a MegaBACE 1000 DNA Sequencer (Amersham Pharmacia Biotech, Piscattaway, USA). The injection parameters were 3 kV for 25 seconds. The run was performed at 9 kV for a total of 120 minutes. The basecaller used was Cimarron Slim Phredify 2.6. With confidence values (Phred20) from Phred. (Brent et al, Genome Research 8:175-185, 1998, and Brent et al, Genome Research 8:186-194, 1998.)

1.2 Results and Discussion

Overview of the Purification and Release of Cycle Sequencing Products

Figure 1:
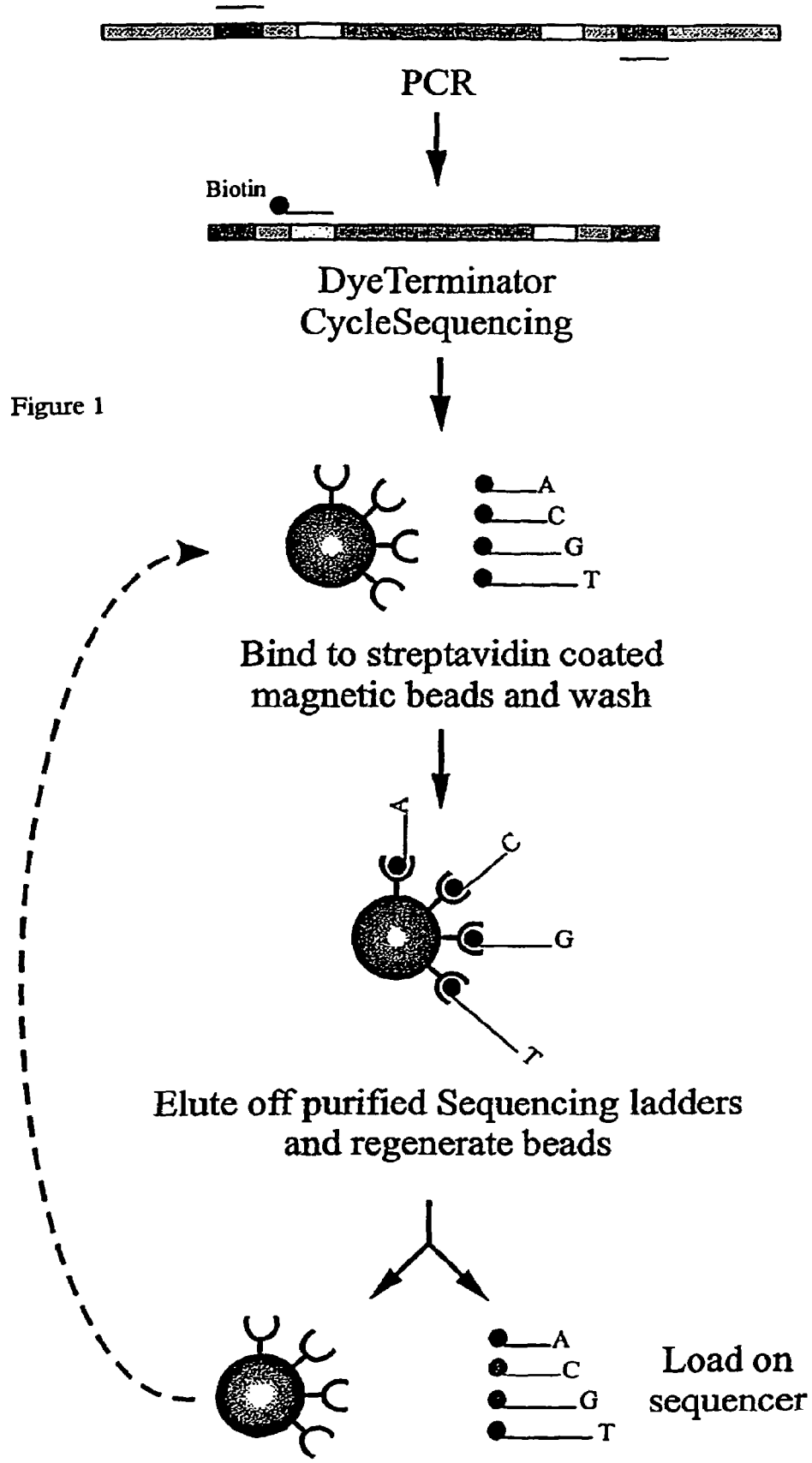
FIG. 1 is a schematic drawing illustrating the principle of the method of Example 1.

The principle of the method described here is outlined in FIG. 1. In general the first stage of the method involves binding of biotinylated DNA onto streptavidin-coated magnetic beads. This is well known and proven to be robust (Hultman et al., Nucleic Acids Res. 17:4937-4946, 1989 and Fangan et al., BioTechniques 26:980-083, 1999). The magnetic bead chosen featured a hydrophilic surface to enable as little non-specific binding to the unincorporated hydrophobic terminator dyes as possible (M270 Streptavidin Dynabeads, Dynal AS, Oslo, Norway). In the second stage, the beads were incubated in water at an elevated temperature (80° C.) to effect non-denaturing release of the cycle sequencing products. Both the streptavidin and the biotin were shown to retain their binding properties following release.

Figure 2:
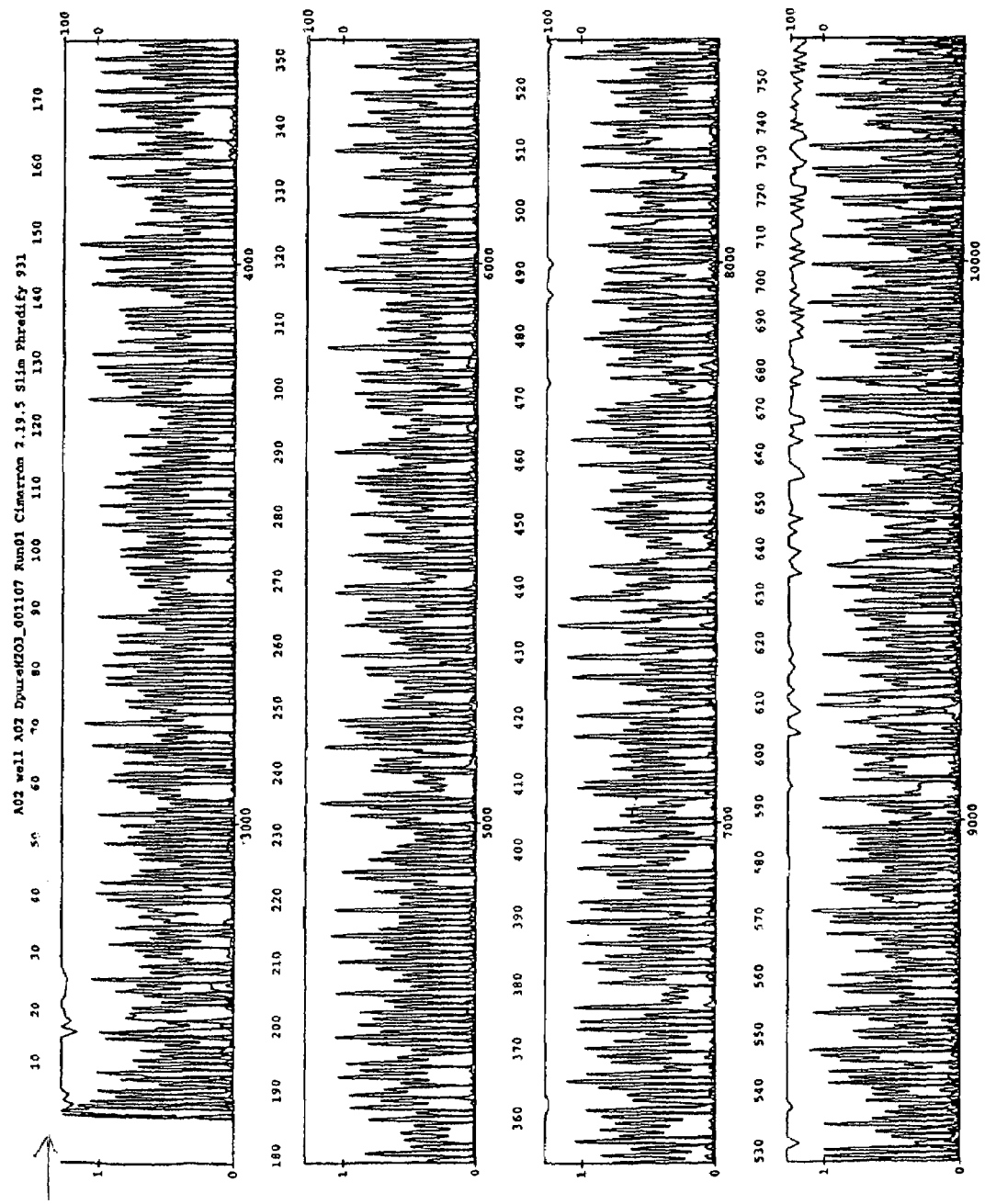
FIG. 2 shows the sequence run result after release in water.
Figure 3:
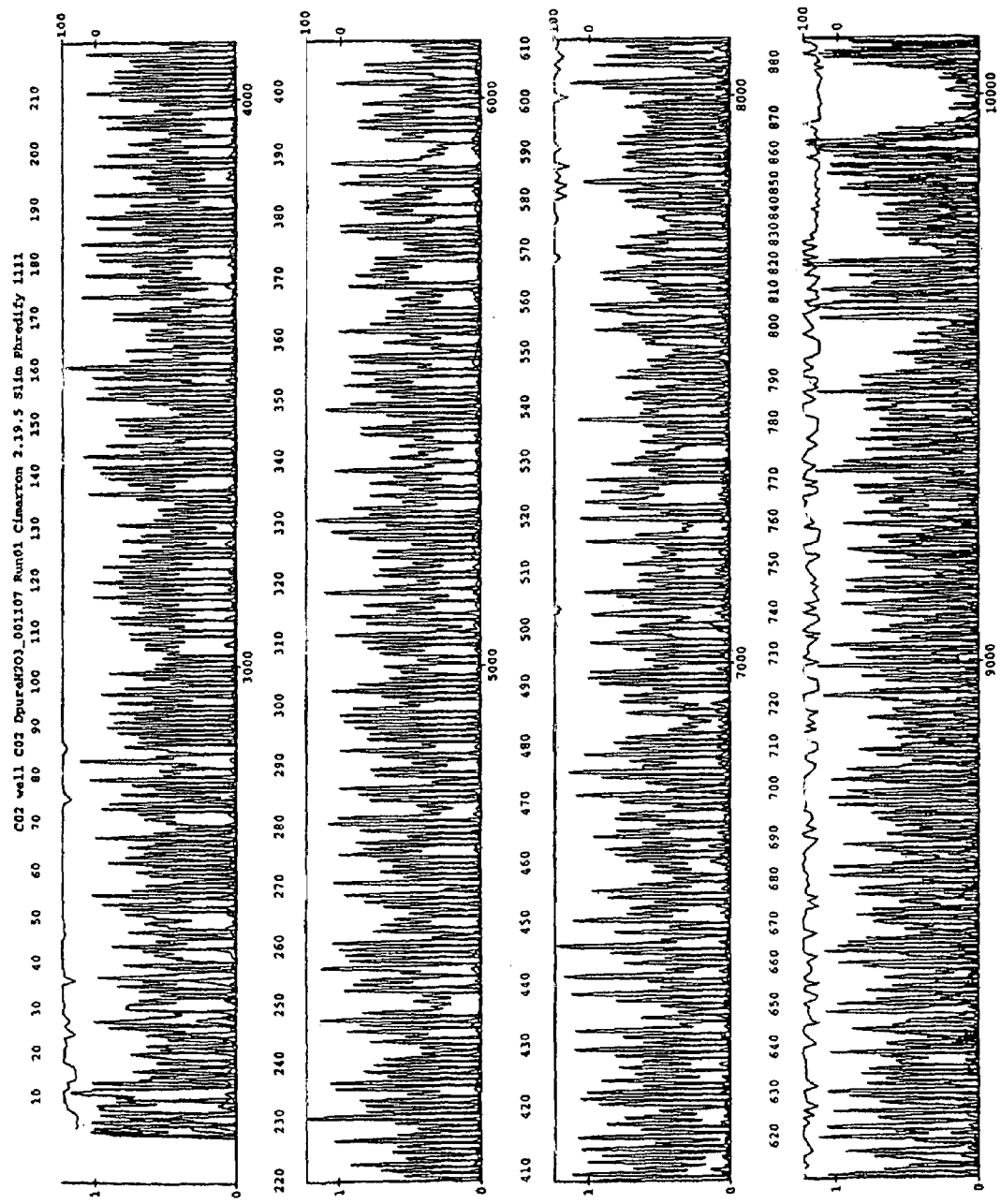
FIG. 3 shows the sequence run result with re-used streptavidin beads.

The released sequencing products were analysed on a MegaBACE capillary sequencer and were found to give a basecalled sequence reading length of approximately 700 bases (FIG. 2). To further investigate if the streptavidin beads retained a binding capacity the beads were re-conditioned in binding buffer and used again for a second round of capture of new sequencing products. FIG. 3 shows the corresponding basecalled sequence result. The read length of approximately 700 bases indicated a similar binding capacity of the streptavidin beads the second time.

Following these findings, we then investigated the released biotin's capacity to again bind to streptavidin.

Initially bound and then released sequencing products were used as samples in a second run. The resulting electropherograms exhibited a very slight decrease in signal strength (up to 5%) probably due to manual interventions, but showed virtually identical read length and base resolutions (FIGS. 4 and 5).

Optimization of Release Buffer, Temperature and Incubation Conditions

The effect of release buffer (EDTA concentration), temperature and incubation time was investigated. EDTA was included in our initial investigations since it was previously shown to be required for effective elution (Tong et al., Anal. Chem. 64:2672-2677, 1992). However, in contrast to previous findings, we demonstrate that it has an adverse effect on elution. Also, we found that EDTA affects the injection phase into the capillary sequencers.

In these experiments we performed a normal capture of sequencing products followed by elution using different concentrations of EDTA at 80° C. (0-20 mM). FIG. 6 shows the corresponding raw data which indicates that even small amounts of EDTA reduce the efficiency in elution and/or injection. To further investigate this a series of cycle sequencing samples already eluted in different EDTA concentrations (as outlined above) were re-captured onto the solid-phase and this time eluted in water. The results (FIG. 7) show that presence of EDTA in the elution step results in lower signals and read-lengths although injection on the sequencer was performed in water. It may be concluded that EDTA affects both the binding/elution to a solid support and injection into capillaries. The conclusion from these experiments was that water alone gave superior results.

Following optimization of the buffer formulation the incubation time and temperature for elution in pure water were investigated. Pools of cycle sequencing products were used for these purposes. First different elution temperatures, ranging from 20° C. to 90° C., were studied by analysis of the data obtained from the MegaBACE sequencer. As shown in FIG. 8 optimal elution was achieved at 80° C. (incubation time was 1 minute in all cases) as determined by comparing average read lengths. However the differences were more pronounced when the signal strengths of the runs were compared. Again, 80° C. was found to be optimal. The effect of incubation time at 80° C. was then investigated and the data presented in FIG. 9. The results show that heating to 80° C. followed by immediate cooling to ambient temperature is sufficient for an efficient elution. Further, we found that incubations for more than one to two minutes gave a significant decrease in read-length and signal strength. This decrease is not considered to arise from degradation of the sequencing products since the cycle sequencing reactions are normally heated to 94° C. for 2-4 minutes prior to loading on a sequencer.

With the optimized conditions we performed analysis on the re-use of streptavidin beads. The same set of beads was used in 6 subsequent cycles of re-use with six different cycle sequencing products. An example of the sequence run result obtained after the sixth cycle of re-use is shown in FIG. 10. Approximately 700 bases were obtained with very low background indicating very efficient elution between subsequent cycles. Indeed experiments have shown that the streptavidin beads can be re-used at least 8 times in the methods of the invention without affecting significantly the read length seen (data not shown).

In conclusion we have shown that streptavidin beads can be successfully used multiple times without loss of efficiency and performance. The possibility to elute biotinylated molecules at relatively mild conditions from the streptavidin support and re-use both the biotin and the streptavidin opens new possibilities for future applications.

EXAMPLE 2

2.1 Materials and Methods

Preparation of PCR-Products

PCR products in the range of 675, 900 and 1150 bp were generated using standard condition 50 µl PCR reactions (10 mM Tris-HCl (pH 8.3), 5 mM KCl, 2 mM $MgCl_2$ 0.2 mM of each DNTP, 0.5 U AmpliTaq DNA polymerase (Perkin-Elmer, Norwalk, Conn., USA) and 5 pmol of biotinylated USP (universal sequencing primer) and 5 pmol of RSP (reverse sequencing primer)) using a PTC 225 Thermocycler (MJ Research, Waltham, Mass., USA).

Capture and Elution of Biotinylated Cycle Sequencing Products

For each experiment, 100 µg of M270 Streptavidin beads (Dynal AS, Oslo, Norway) were used. The beads were initially captured once and resuspended in 20 µl of 2×B/W buffer (10 mM Tris-HCl (pH 7.5), 1 mM EDTA, 2M NaCl, 0.1% Tween 20) and transferred to 20 µl of PCR product. After 15 minutes incubation at room temperature with three intermittent mixes, the beads with captured dsDNA were magnetically collected and rinsed twice with 1×TE (10 mM Tris-HCl (pH 7.5), 1 mM EDTA) to remove any impurities and salts from the PCR reaction and binding buffer. Following the wash procedure, the beads were resuspended in 20 µl of the current test solution and incubated at various temperatures and for different times according to the current test criteria (i.e. the conditions studied). After incubation the beads were magnetically collected and the supernatant transferred to a new tube and saved for analysis. The beads were then resuspended in 20 µl purified water and the temperature increased to 80° C. with roughly 1° C. increase every 2 seconds (i.e. optimized conditions). This was followed by cooling to ambient temperature. The beads were then magnetically collected and the supernatant transferred to a new tube and saved for analysis.

This procedure permitted (i) the determination of the amount of biotinylated dsDNA released during the conditions studied and (ii) the determination of the amount of dsDNA remaining bound to the beads (removed under the optimized conditions of pure water at 80° C. for 1 second).

The following parameters and conditions were tested:

1. Temperature and time: 20-80° C. (10° C. intervals) at 1, 10, 30, 60, 120 and 300 seconds
2. pH: 6, 7, 8, 9 and 10 (10 mM Tris)
3. EDTA: 0.25, 1.0, 5.0, 10 and 50 mM
4. NaCl: 10, 25, 50, 100 and 500 mM
5. Tris: 1, 10, 50 and 100 mM (pH 7.5)
6. TE buffer: 0.5×, 1×, 5× and 10×
7. LiCl and $MgCl_2$: 10 and 100 mM All results were first screened using agarose gels as a standard control method.

Evaluation Using Agilent 2100 Bioanalyzer

The relative amount of released dsDNA was evaluated using an Agilent 2100 Bioanalyzer (Agilent Technologies, Palo Alto, Calif., USA) using the DNA7500 LabChip, or the DNA1000 LapChip. Experiments were performed according to the manufacturer's instructions. Minimum peak height was globally set to 2.0 for the DNA7500 chip and 1.0 for the DNA1000 chip.

The results on the Bioanalyzer and the agarose gels were consistent at all times.

2.2. Results and Discussion

Results are shown in attached FIGS. 11-24.

Figure 11:
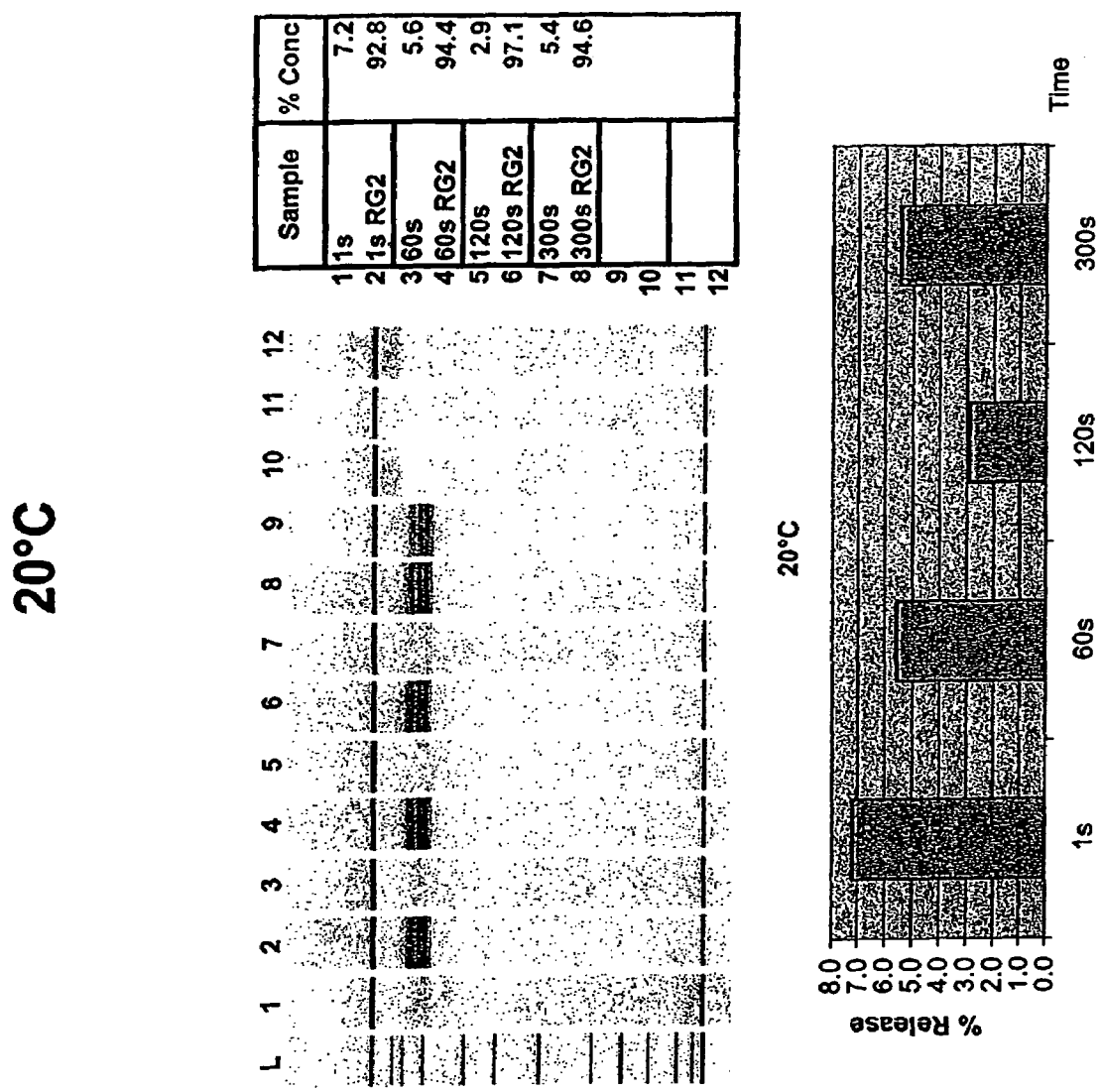
Figure 12:
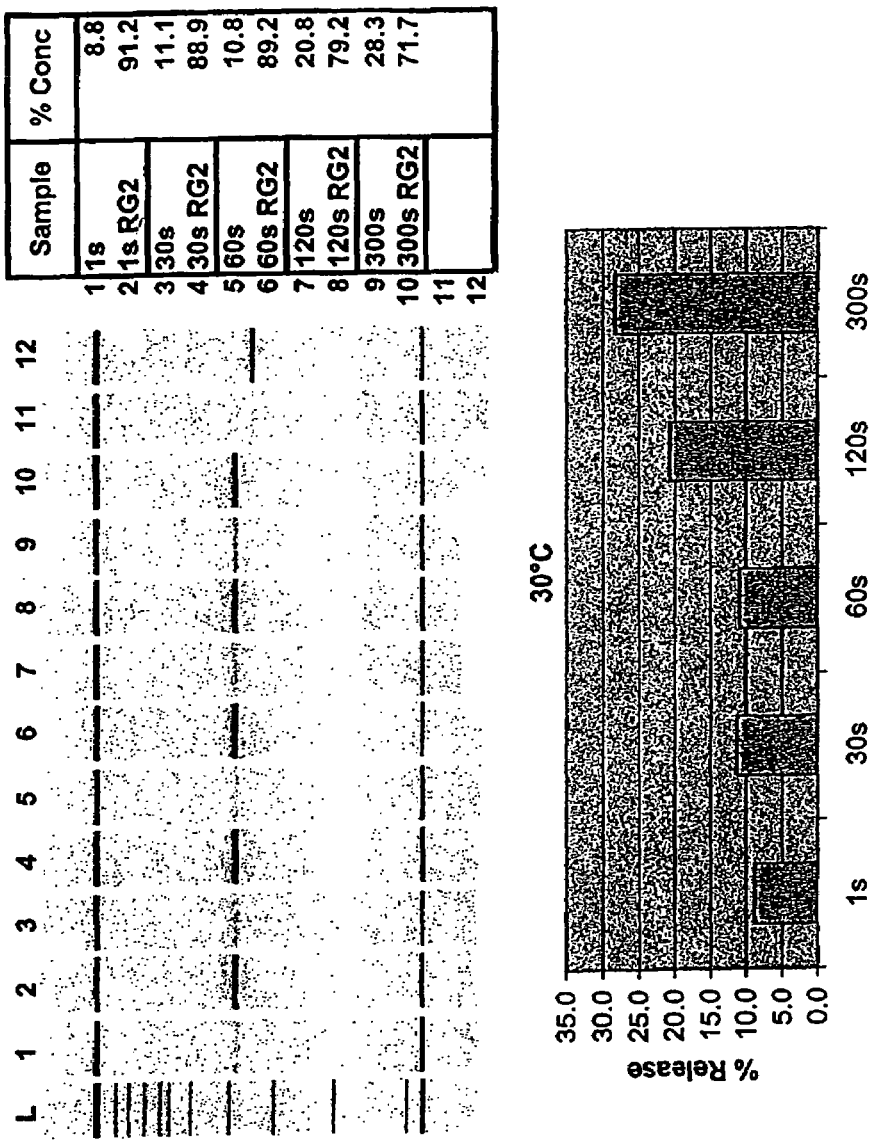
Figure 13:
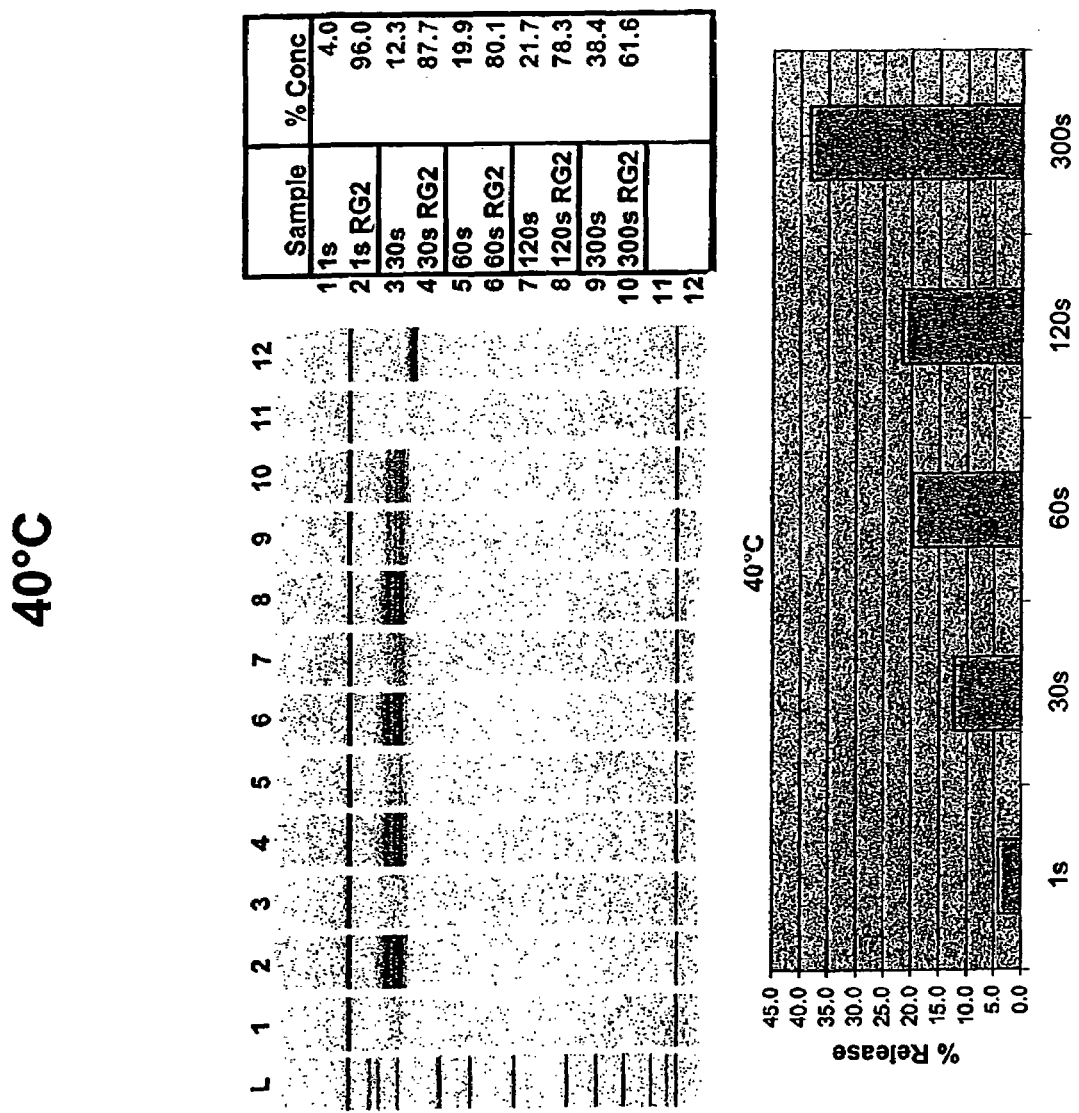
Figure 14:
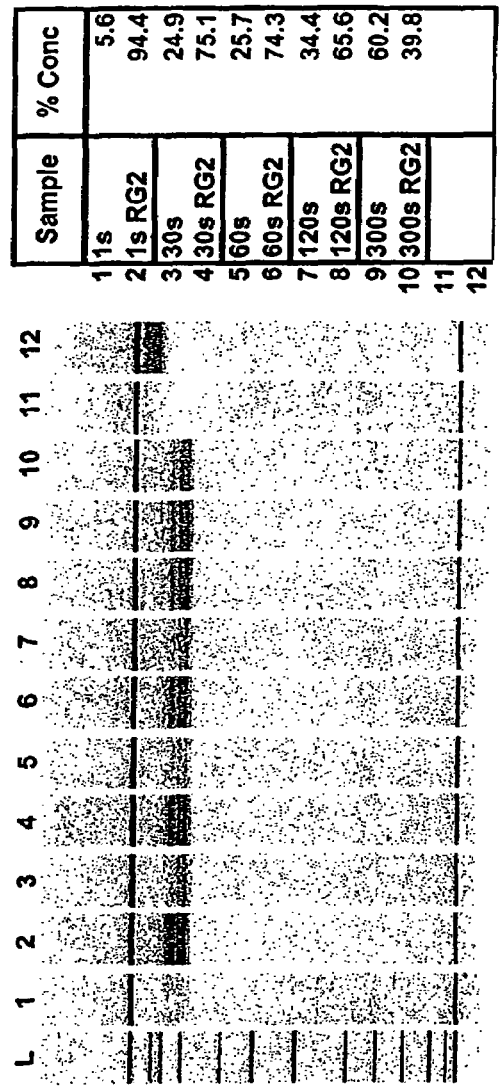
Figure 14:
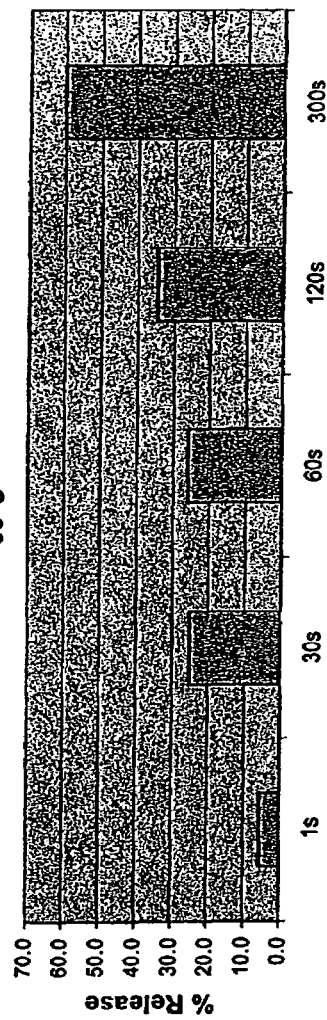
Figure 15:
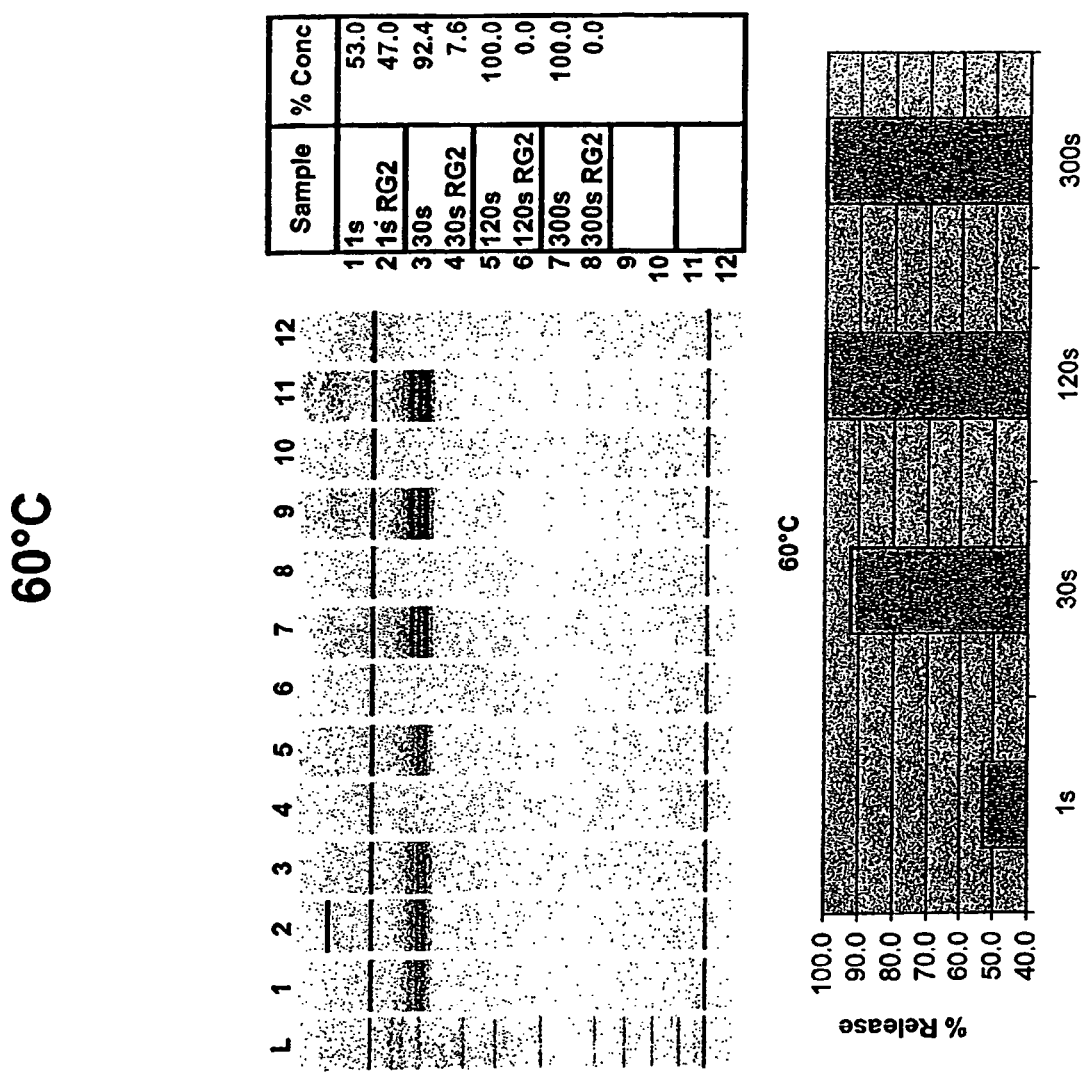
Figure 16:
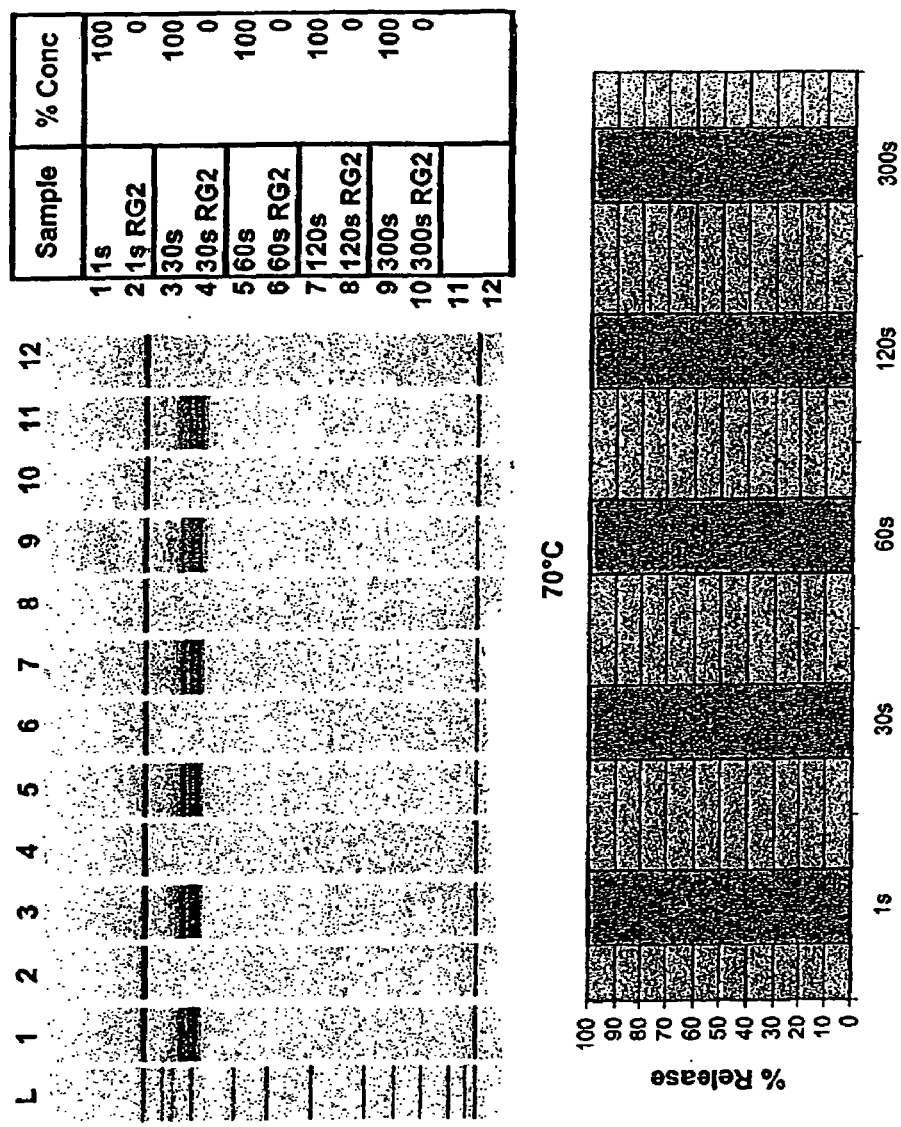
Figure 17:
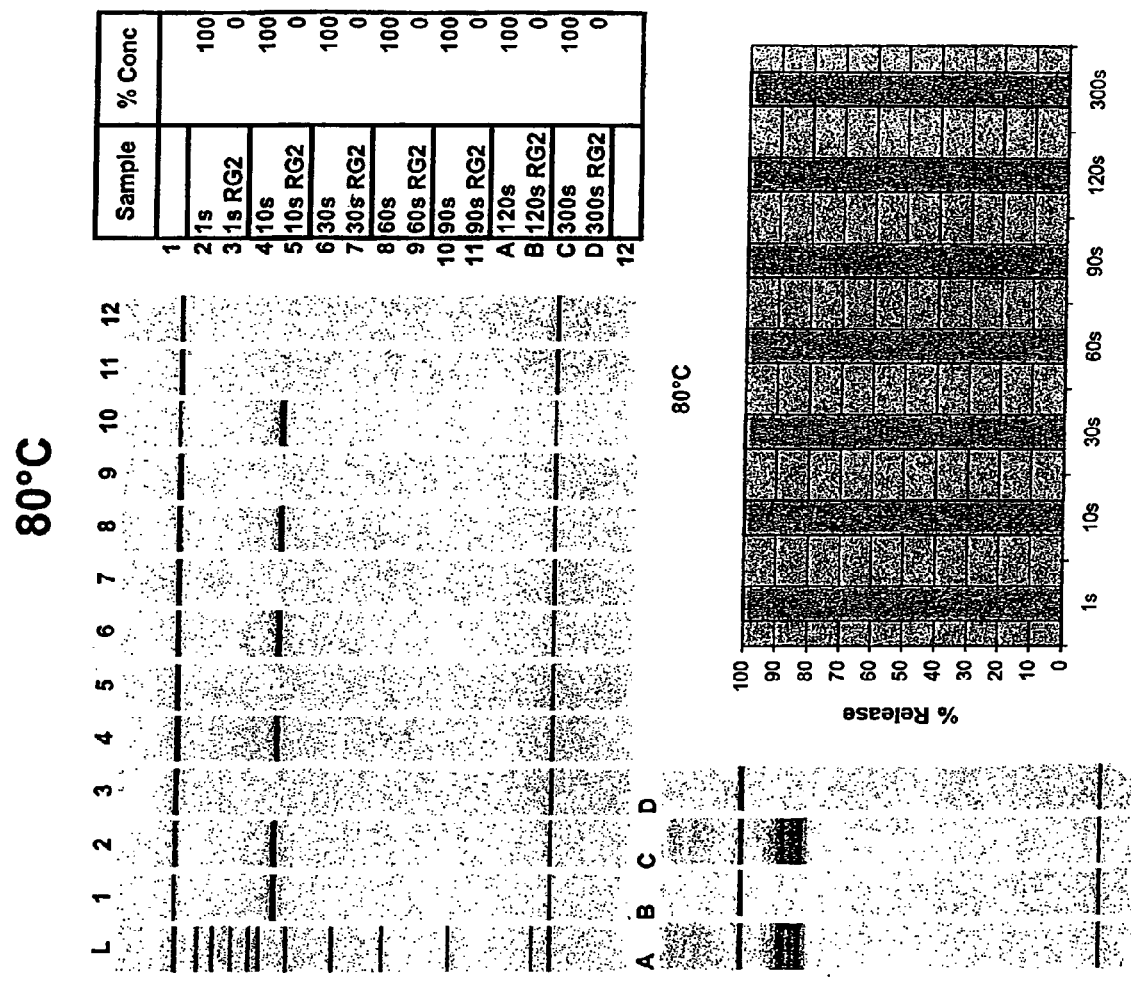
Figure 18:
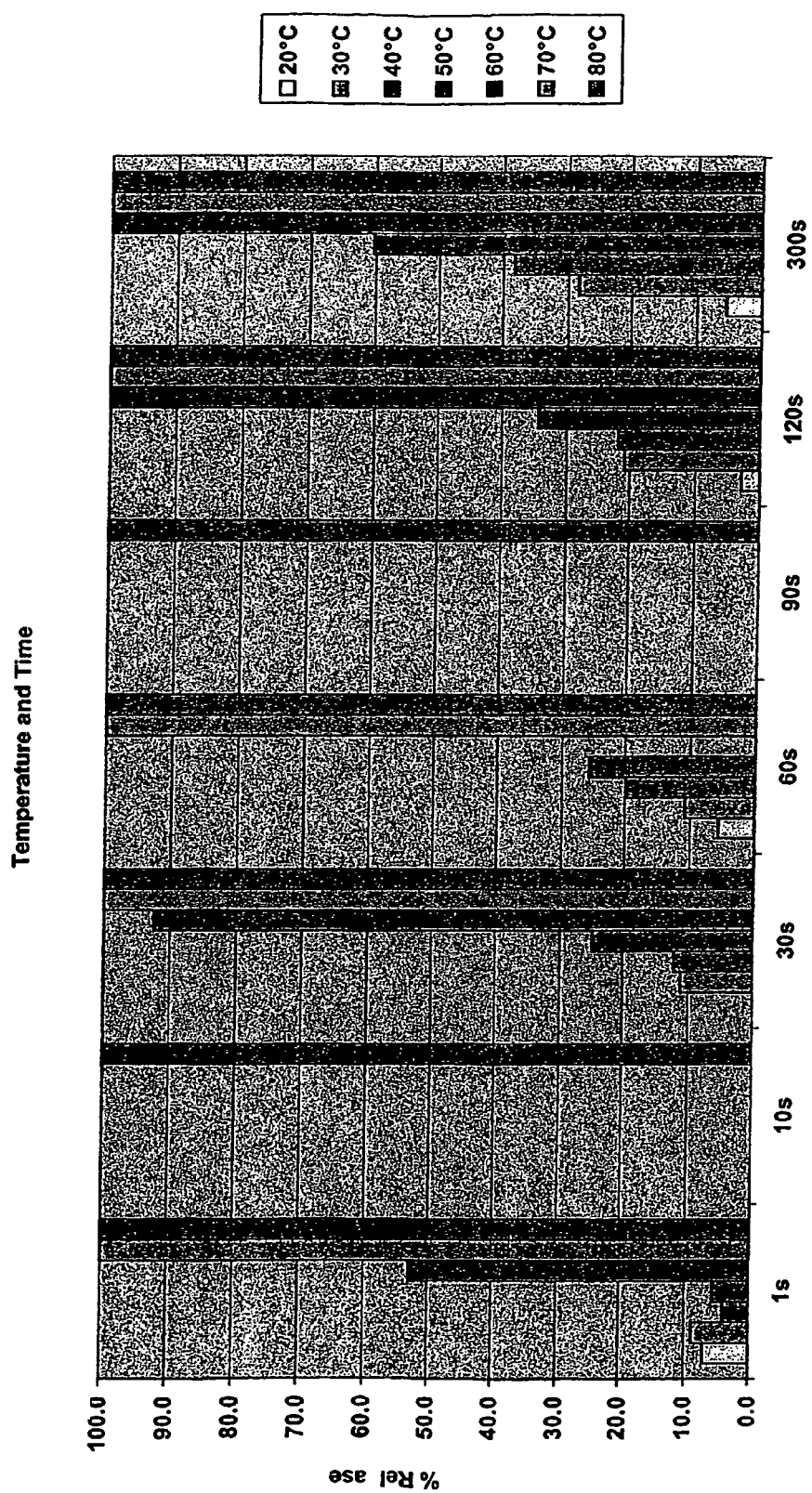

As shown in FIG. 11, at room temperature (20° C.) a small fraction of the dsDNA is released in pure water (approx. 3-8%). This seems to be consistent over all incubation times tested (i.e. from 1 to 300 seconds). At 60° C. (see FIG. 15), 50% is immediately released, after 30 seconds about 90% and after approx. 120 seconds, 100%. At temperatures above 70° C., 100% is released immediately.

As shown in FIG. 19, variation in pH appears to have little significant effect in the range 6-10 (10 mM Tris). A slight amount of remaining DNA was detected in the pH range 6-8. However, this is probably due to the Tris-HCl buffer and the salt components resulting from re-titrations using NaOH rather than the pH.

0.25 and 1 mM EDTA appear to have little effect on the release (see FIG. 20). 5 mM EDTA gave a very slight decrease in one of the repeats (approx. 1%). An EDTA concentration from 10-50 mM results in a decrease in the release from 85 to 50%.

At higher concentrations of NaCl, a clear decrease in the efficiency of release at higher concentrations is observed (see FIG. 21). About 90% is eluted at 10 mM with an almost linear drop to 30% at 100 mM.

As shown in FIG. 22, 1 mM Tris seems to have little effect on the efficiency of release. At a concentration of 10 mM Tris, the efficiency falls by a few percent. At 50 and 100 mM Tris the efficiency of release falls to about 50%.

FIG. 23 shows the effect on release of the combination of Tris and EDTA at its most commonly used concentration (1×TE: 1 mM EDTA; 10 mM Tris, pH 7.5). Interestingly, it was found that this combination (1×TE) results in only a 90% release.

FIG. 24 shows the effect on release of the salts LiCl and $MgCl_2$. LiCl exhibited an effect similar to that found for NaCl. However, $MgCl_2$ resulted in only 10% release at 10 mM (cf. 90% for LiCl and NaCl).

---

The invention claimed is:

1. A method of reversibly disrupting a conjugate comprising a biotin compound and a biotin-binding compound, said method comprising the step of contacting said conjugate with an effective amount of a substantially aqueous solution comprising less than 100 mM sodium chloride at a temperature of from 50 to 90° C. under conditions such that the conjugate is disrupted, thereby forming a biotin compound and a biotin-binding compound, wherein the biotin-binding compound is streptavidin, avidin or a derivative or analog thereof which is capable of binding to said biotin compound.

2. The method of claim 1 wherein said conjugate comprises a biotin-avidin or biotin-streptavidin linkage.

3. The method of claim 1, wherein said substantially aqueous solution contains at least 50% by volume of water.

4. The method of claim 1, wherein said substantially aqueous solution is substantially free of chelating agents.

5. The method of claim 1, wherein said substantially aqueous solution is substantially free of monovalent and/or divalent salts.

6. The method of claim 1, wherein said substantially aqueous solution is purified or distilled water.

7. The method of claim 1, wherein said contacting step comprises incubation of said conjugate at a temperature in the range of from about 60 to 90° C.

8. The method of claim 1, wherein said contacting step comprises incubation of said conjugate at a temperture of about 80° C.

9. The method of claim 1, wherein said biotin compound is bound or linked to one or more biological or chemical entity.

10. The method of claim 9, wherein said biological entity is a nucleic acid molecule, a protein or a chimeric molecule comprising a nucleic acid or protein.

11. The method of claim 1, wherein either the biotin or biotin-binding compound is immobilised on a solid support.

12. The method of claim 11, wherein the biotin-binding compound is immobilised.

13. The method of claim 11, or claim 12 wherein the solid support is particulate.

14. The method of claim 13, wherein said solid support comprises magnetic beads.

15. The method of claim 11, wherein the surface of said solid support is substantially hydrophilic.

16. The method of claim 11, wherein following disruption of said conjugate the solid support is re-used one or more times.

17. The method of claim 11, further comprising the additional step of re-conditioning the solid support so that the support can be re-used.

18. A method of reversibly releasing a biotinylated moiety from a support comprising a biotin-binding compound, said method comprising the step of eluting said support with a substantially aqueous solution comprising less than 100 mM sodium chloride at a temperature of from 50 to 90° C., whereby to effect release of said moiety, wherein the biotin-binding compound is streptavidin, avidin or a derivative or analog thereof which is capable of binding to said biotin compound.

19. A method of reversibly immobilising a biotinylated moiety, said method comprising the following steps:
   (a) binding said biotinylated moiety to a support comprising a biotin-binding compound, and subsequently
   (b) eluting said support with a substantially aqueous solution comprising less than 100 mN sodium chloride at a temperature of from 50 to 90° C., whereby to effect release of said biotinylated moiety, wherein the biotin-binding compound is streptavidin, avidin or a derivative or analog thereof which is capable of binding to said biotin compound.

20. The method of claim 18 or 19 wherein said substantially aqueous solution is purified or distilled water.

* * * * *

SEQUENCE LISTING

<160> NUMBER OF SEQ ID NOS: 3

<210> SEQ ID NO 1
<211> LENGTH: 23
<212> TYPE: DNA
<213> ORGANISM: Artificial
<220> FEATURE:
<223> OTHER INFORMATION: RIT 27 PCR Primer

<400> SEQUENCE: 1
gcttccggct cgtatgttgt gtg                23

<210> SEQ ID NO 2
<211> LENGTH: 23
<212> TYPE: DNA
<213> ORGANISM: Artificial
<220> FEATURE:
<223> OTHER INFORMATION: RIT 28 PCR Primer

<400> SEQUENCE: 2 aaaggggat gtgctgcaag gcg                23

<210> SEQ ID NO 3
<211> LENGTH: 21
<212> TYPE: DNA
<213> ORGANISM: Artificial
<220> FEATURE:
<223> OTHER INFORMATION: M13 PCR Primer

<400> SEQUENCE: 3
cacacaggaa acagctatga c                 21